(12) United States Patent
Shinzato et al.

(10) Patent No.: US 12,717,214 B2
(45) Date of Patent: Aug. 25, 2026

(54) OPTICAL DEVICE AND ENDOSCOPE

(71) Applicant: OLYMPUS CORPORATION, Tokyo (JP)

(72) Inventors: Jun Shinzato, Musashino (JP); Seiji Sakai, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 298 days.

(21) Appl. No.: 18/526,641

(22) Filed: Dec. 1, 2023

(65) Prior Publication Data

US 2024/0103340 A1 Mar. 28, 2024

Related U.S. Application Data

(63) Continuation of application No. PCT/JP2021/021996, filed on Jun. 9, 2021.

(51) Int. Cl.
*G03B 5/00* (2021.01)
*A61B 1/00* (2006.01)
*A61B 1/045* (2006.01)

(52) U.S. Cl.
CPC .................. *G03B 5/00* (2013.01); *A61B 1/00* (2013.01); *A61B 1/00188* (2013.01); *A61B 1/045* (2013.01); *G03B 2205/0069* (2013.01)

(58) Field of Classification Search
None
See application file for complete search history.

(56) References Cited

U.S. PATENT DOCUMENTS 5,359,992 A 11/1994 Hori et al.
2020/0166740 A1 5/2020 Nagamizu

FOREIGN PATENT DOCUMENTS

| | | | |
|---|---|---|---|
| JP | S501750 | A | 1/1975 |
| JP | H04254 | B2 | 1/1992 |
| JP | 3085410 | B2 | 9/2000 |
| JP | 2002-258165 | A | 9/2002 |
| JP | 2008-194326 | A | 8/2008 |
| JP | 2009-160276 | A | 7/2009 |
| JP | 4960115 | B2 | 6/2012 |
| JP | 5144281 | B2 | 2/2013 |
| JP | 2020-151101 | A | 9/2020 |
| WO | 2019/026445 | A1 | 2/2019 |

OTHER PUBLICATIONS

International Search Report dated Jul. 20, 2021 received in PCT/JP2021/021996.

*Primary Examiner* — Richard H Kim
(74) *Attorney, Agent, or Firm* — Scully, Scott, Murphy & Presser, P.C.

(57) ABSTRACT

An optical device includes: an optical system including a moving lens that moves in a direction along an optical axis; a moving frame including a first magnetic body and configured to hold the moving lens; a holding frame formed into a cylindrical shape by a non-magnetic body and configured to movably hold the moving frame on an inner circumferential surface along the optical axis; a drive unit including a magnet and configured to cause the moving frame to move in the direction along the optical axis; and second magnetic bodies arranged between the drive unit and the moving frame and configured to transmit a magnetic force of the magnet to the first magnetic body of the moving frame.

19 Claims, 14 Drawing Sheets

37
31
33
32
34
41
35E
42
A
B
C
6a
6E
37a

OPTICAL DEVICE AND ENDOSCOPE

CROSS REFERENCE TO RELATED APPLICATION

This application is a continuation application of PCT/JP2021/021996 filed on Jun. 9, 2021, the entire contents of which are incorporated herein by this reference.

BACKGROUND OF THE INVENTION

1. Field of the Invention

The present invention relates to an optical device including a switching mechanism that switches a focal position or a focal length and an endoscope to which the optical device is applied.

2. Description of the Related Art

Conventionally, endoscopes configured to include insertion portions with elongated pipe shapes have widely been used in the medical field and the industrial field, for example. Particularly, medical endoscopes used in the medical field have a function of observing inside of living bodies, such as organs by inserting insertion portions including observation units into body cavities of the living bodies, for example. Also, the medical endoscopes are configured to be able to perform various treatments on target organs or the like by using a predetermined treatment instrument as needed. Industrial endoscopes used in the industrial field are configured to be able to observe and inspect states, such as scratches and corrosion, inside devices or mechanical facilities, such as jet engines and factory piping, for example, by inserting insertion portions including observation units into the devices, the mechanical facilities, and the like.

An observation unit in a conventional endoscope in the form of this type is configured of an optical device or the like including, for example, an optical system unit and an image pickup unit. The optical system unit is configured of a plurality of optical lenses and the like that form an optical image of an observation target on a predetermined image-forming plane. The image pickup unit is configured to include an image pickup device that receives light of an optical image of the observation target formed by the optical system unit, performs predetermined photoelectric conversion processing, and generates an image signal, an image pickup signal processing circuit that performs predetermined signal processing on the image signal generated by the image pickup device and generates image pickup data in a predetermined form, and the like. Also, in the conventional endoscope, the aforementioned optical device and the like are typically configured to be arranged inside a distal end portion of a configuration member of the insertion portion of the endoscope on the side closest to the distal end.

Also, some optical devices applied to the conventional endoscopes have moving lenses obtained by configuring some optical lenses from among a plurality of optical lenses configuring optical system units to be movable along optical axes. Therefore, such an optical device including the moving lens is required to include a drive unit for causing the moving lens to move at a predetermined appropriate timing along the optical axis. Then, the drive unit is used to cause the moving lens to move in a direction along the optical axis. The drive unit can thus have a function of switching a focal length of the entire optical system unit and a function of switching a focal position and performing focal point adjustment.

As the optical devices in the form of this type, that is, optical devices including moving lenses and having a focal point switching function or a focal point adjustment function, Japanese Patent Application Laid-Open Publication No. 2002-258165 and Japanese Patent No. 3085410, for example, have proposed various optical devices.

The optical device disclosed in Japanese Patent Application Laid-Open Publication No. 2002-258165 described above has a function of controlling a drive unit configured of an actuator to cause the drive unit to drive focal position adjustment means, causing a holding frame holding some of moving lenses of an optical system to move in a direction along an optical axis, and thereby performing a focal point adjustment operation.

Also, the optical device disclosed in Japanese Patent No. 3085410 described above is configured such that a lens holding frame holding some of moving lenses of an optical system unit is formed of a ferromagnetic body and an annular permanent magnet is provided to surround the surroundings of the lens holding frame. Also, the permanent magnet is configured to move in a direction along an optical axis in conjunction with a rotating operation of an operation ring. With the configuration, the permanent magnet moves in the direction along the optical axis when the operation ring is operated to rotate in the optical device. With the movement of the permanent magnet in the optical axis direction, the lens holding frame of the ferromagnetic body also moves in the same direction. Thus, the moving lens moves in the optical axis direction, and focal point adjustment is performed. With the configuration, the magnet that moves in the optical axis direction in conjunction with the operation ring and the lens holding frame configured of the ferromagnetic body function as a drive unit that causes the moving lens to be driven.

On the other hand, Japanese Patent No. 5144281, for example, has proposed optical devices in each of which an optical system unit including a moving lens, an image pickup unit, and a drive unit are integrally configured, as optical devices that are applied to the conventional endoscopes. Note that the optical device disclosed in Japanese Patent No. 5144281 described above is configured by using a magnet as a member configuring the drive unit of the moving lens.

SUMMARY OF THE INVENTION

An optical device according to an aspect of the present invention includes: an optical system including a moving lens that moves in a direction along an optical axis; a moving frame including a first magnetic body and configured to hold the moving lens; a holding frame formed into a cylindrical shape by a non-magnetic body and configured to movably hold the moving frame on an inner circumferential surface along the optical axis; a drive unit including a magnet and configured to cause the moving frame to move in the direction along the optical axis; and second magnetic bodies arranged between the drive unit and the moving frame, configured to transmit a magnetic force of the magnet to the first magnetic body of the moving frame, and provided in a same number as a number of focal points that can be set as adjustment targets of the optical system.

An endoscope according to an aspect of the present invention includes: an optical system including a moving lens that moves in a direction along an optical axis; a moving frame including a first magnetic body and configured to hold the moving lens; a holding frame formed into a cylindrical shape by a non-magnetic body and configured to movably hold the moving frame on an inner circumferential surface along the optical axis, a drive unit including a magnet and configured to cause the moving frame to move in the direction along the optical axis; second magnetic bodies arranged between the drive unit and the moving frame, configured to transmit a magnetic force of the magnet to the first magnetic body of the moving frame, and provided in a same number as a number of focal points that can be set as adjustment targets of the optical system; and a conduit line or an illumination device arranged between the drive unit and the moving frame.

DETAILED DESCRIPTION OF THE PREFERRED EMBODIMENT

Figure 1:
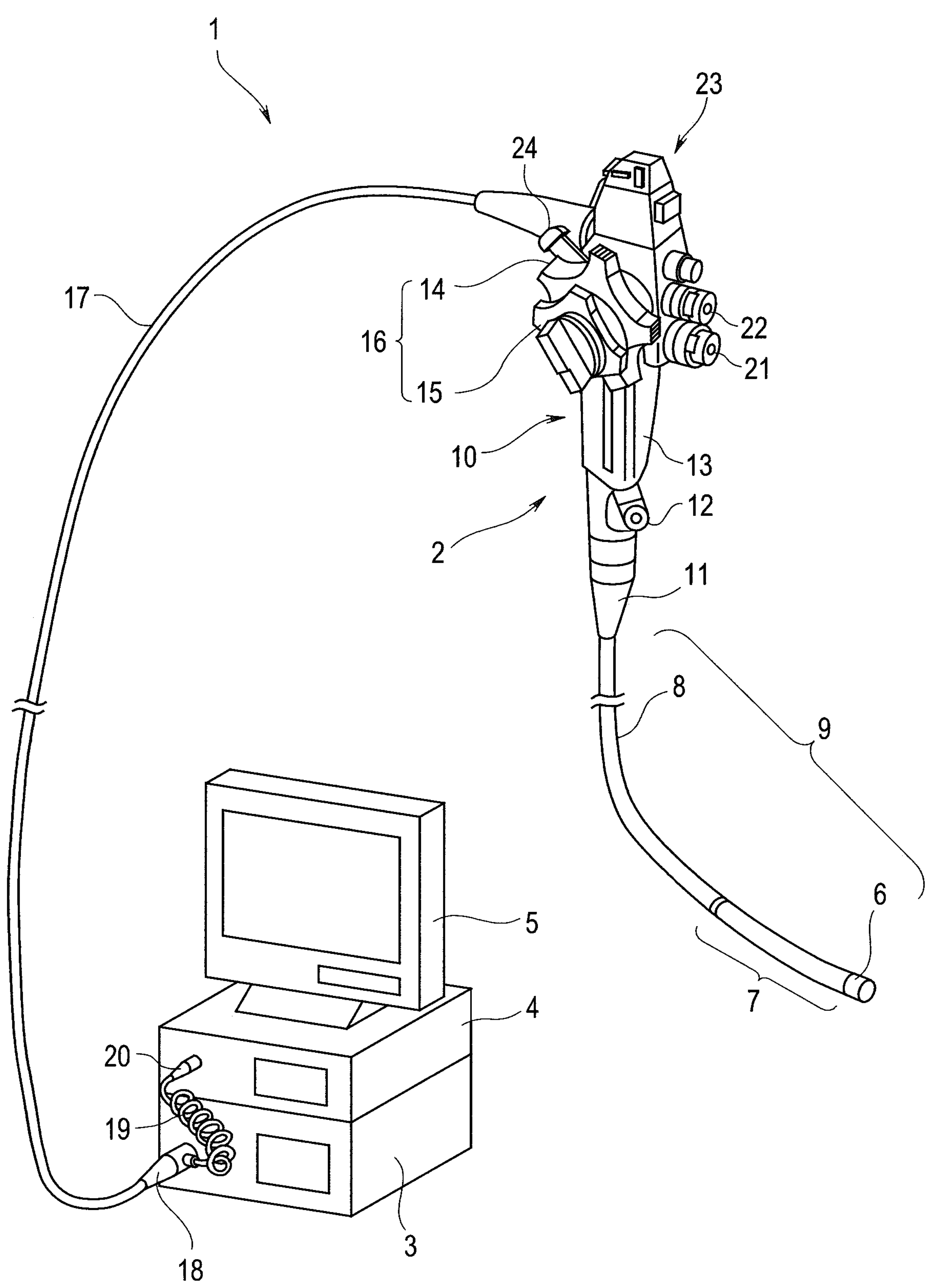
FIG. 1 is an external view illustrating an endoscope system that includes an endoscope to which an optical device according to an embodiment of the present invention is applied.

In a conventional optical device, it is typically necessary to arrange an optical system unit including a moving lens and a drive unit to be close to each other in order to reliably cause the moving lens to move in a direction along an optical axis. If the optical system unit including the moving lens and the drive unit are arranged at separated positions, for example, it may not be possible to efficiently transmit a drive force of the drive unit to the moving lens.

Also, the conventional endoscope with a typical configuration typically includes a cleaning unit including a cleaning nozzle for spraying a cleaning solution onto and cleaning a front surface of an optical member (observation window) of the optical system unit on the side closest to the distal end, an illumination unit that illuminates, with illumination light, an observation target that is present in front of the distal end portion of the endoscope, and the like.

In order for the cleaning unit to effectively clean the front surface of the observation window and the like in the endoscope in the form of this type, it is desirable that the cleaning nozzle be arranged at a position in the vicinity of the observation window of the optical system unit in the front surface at the distal end portion of the endoscope. To do so, it is desirable that a cleaning solution supply pipe of the cleaning unit and the optical system unit be disposed at positions that are close to each other in an internal configuration at the distal end portion of the endoscope, for example.

In consideration of the matters, the configurations of the conventional optical devices disclosed in Japanese Patent Application Laid-Open Publication No. 2002-258165 described above, Japanese Patent No. 3085410 described above, Japanese Patent No. 5144281 described above, and the like may cause a problem that arrangement of members inside the distal end portions of the endoscopes are limited. The problem may lead to inhibition of diameter reduction and size reduction of the endoscopes.

Also, the conventional optical device disclosed in Japanese Patent No. 5144281 described above has problems that the overall configuration may be complicated due to the optical system unit, the image pickup unit, and the drive unit being integrally configured and that the optical device itself may increase in size.

Typically, a procedure of arranging the driving unit, the cleaning unit, and the like around the optical axis of the optical system unit in the optical device with reference to arrangement of the optical device including the image pickup unit first is adopted when arrangement of the members inside the distal end portion of the endoscope is determined.

Since optimal arrangement of members is considered in accordance with various applications of the conventional endoscope, the arrangement of each configuration unit differs depending on the type of the endoscope. Therefore, if the optical device is configured with the respective configuration units integrated, a problem that the optical device cannot commonly be used by various endoscopes may occur.

Also, the optical device including the respective configuration units as an integrated configuration has a problem that there are many processes of manufacturing the respective configuration units and then integrally assembling the configuration units and processes performed when the integrally configured optical device is assembled with the distal end portion of the endoscope and many processes are needed.

Furthermore, the optical device including the respective configuration units as an integrated configuration also has a problem that even in a case where any one configuration unit out of the respective configuration units breaks down, for example, replacement or the like of the entire optical device is needed.

According to the present invention, it is possible to provide an optical device that is capable of realizing simplification of a structure and improvement in efficiency of assembly, improves a degree of freedom in arranging members inside a distal end portion of an endoscope, and realizes size reduction.

Also, according to the present invention, it is possible to provide an endoscope that has a smaller size, contributes to manufacturing cost reduction, and has excellent maintainability by applying the above optical device.

Hereinafter, the present invention will be described on the basis of the embodiment illustrated in the drawings.

Each drawing used in the following description provides schematic illustration, and each member may be illustrated with a different dimensional relationship, scale, and the like depending on each component in order to illustrate each component with such a size that the component can be recognized in the drawing. Therefore, the present invention is not limited only to the forms illustrated in the drawing in regard to the number of the respective components, the shape of each component, the size ratio, the relative positional relationship of each component, and the like described in each drawing.

First, before describing a detailed configuration of an optical device according to an embodiment of the present invention, a schematic configuration of an endoscope to which the optical device according to the present embodiment is applied will be briefly described below by using FIGS. 1 and 2.

FIG. 1 is an external view illustrating an endoscope system including the endoscope to which the optical device according to the embodiment of the present invention is applied. FIG. 2 is a conceptual diagram illustrating, in a simplified manner, main internal configuration members of the endoscope to which the optical device according to the present embodiment is applied. Note that illustration of some of configuration members that are not directly related to the present invention from among the configuration members provided on an outer surface of the endoscope is omitted or some of the configuration members are illustrated by dotted line and are illustrated in a simplified manner in FIG. 2.

In addition, a basic configuration of the endoscope system to which the optical device according to the present embodiment is applied is substantially the same as the basic configuration of the conventional endoscope system. Therefore, detailed description of each configuration member is omitted and only schematic description will be given in the following description.

As illustrated in FIG. 1, an endoscope system 1 including an endoscope to which the optical device according to the present embodiment is applied is configured of an endoscope 2, a light source device 3, a video processor 4, a color monitor 5, and the like.

Figure 2:
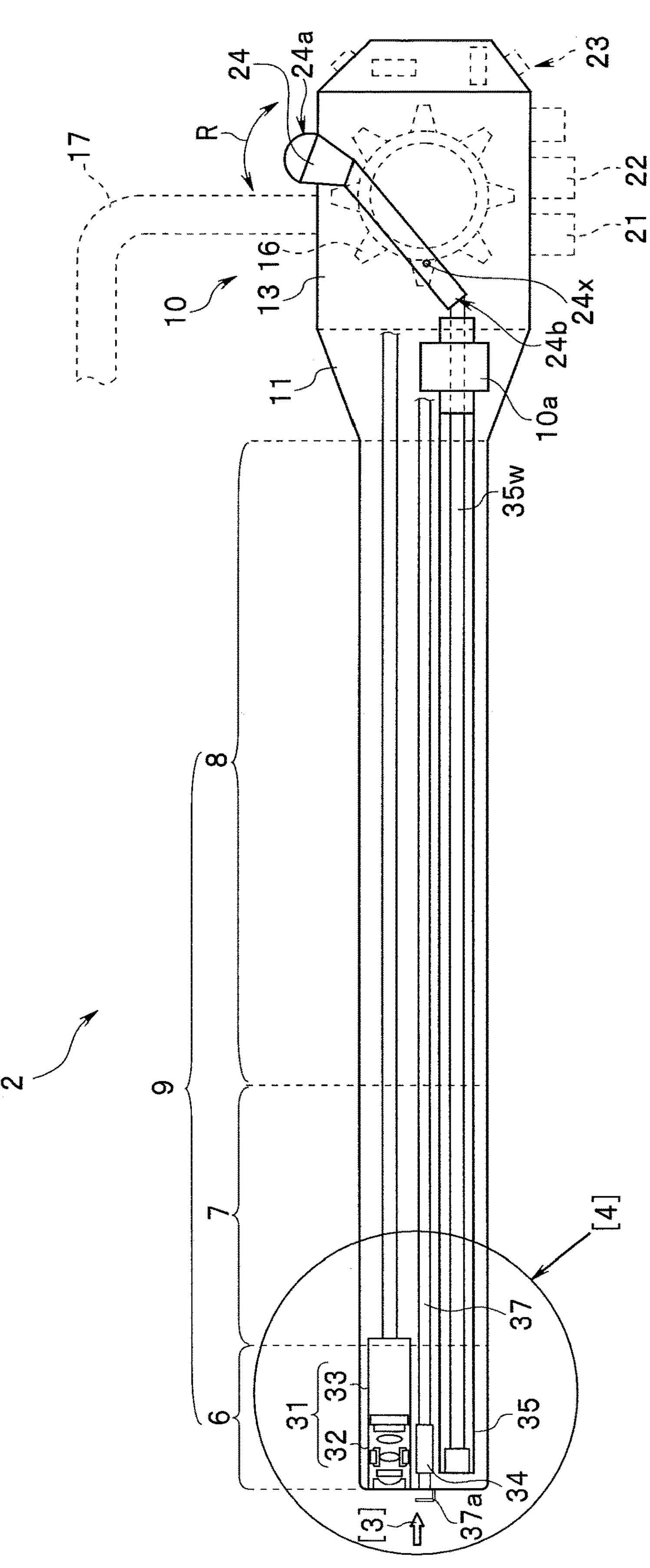
FIG. 2 is a conceptual diagram illustrating an internal configuration of the endoscope in FIG. 1 in a simplified manner.

The endoscope 2 is configured to include an insertion portion 9 with a substantially elongated pipe shape and an operation portion 10 with a substantially box shape, from which the insertion portion 9 extends, as illustrated in FIGS. 1 and 2. Also, a universal cord 17 extends from the operation portion 10 toward a side. A scope connector 18 is provided at a distal end part of the universal cord 17. The scope connector 18 is connected to the light source device 3.

Also, a scope cable 19 extends from the scope connector 18 toward a side. An electric connector portion 20 is provided at a distal end part of the scope cable 19. The electric connector portion 20 is connected to the video processor 4.

The insertion portion 9 of the endoscope 2 is configured such that a distal end portion 6, a bending portion 7, and a flexible tube portion 8 are continuously provided in the order from the side of the distal end.

Various configuration units configuring the optical device according to the present embodiment are disposed at the respective predetermined positions inside the distal end portion 6. The various configuration units configuring the optical device according to the present embodiment includes an observation unit 31 (an optical system unit 32, an image pickup unit 33), a drive unit 35, and the like as illustrated in FIG. 2, for example. In addition to the configuration units, a part of a cleaning unit (a distal end part of a cleaning solution supply pipe 37), a part of an illumination unit (not illustrated), a part of a treatment instrument channel (not illustrated), and the like are arranged inside the distal end portion 6.

The operation portion 10 is configured to include a folding stop portion 11 that is provided at a part from which a proximal end portion of the insertion portion 9 extends, a forceps port 12 (see FIG. 1; not shown in FIG. 2) including an opening into which a treatment instrument or the like is inserted, an operation portion main body 13 configuring a grasping portion, a bending operation portion 16 (see FIG. 1; illustrated in an abbreviated manner in FIG. 2) including two bending operation knobs 14 and 15 that are operation portions for performing upper, lower, left, and right bending operations on the bending portion 7, an air/water feeding control portion 21, a suction control portion 22, a switch portion 23 that includes a plurality of switches and is operated mainly for realizing an image pickup function, an operation lever 24 that executes a focal point adjustment function (focusing function) or a focal length switching (optical enlarged observation) function, and the like.

Note that although details will be described later, the operation lever 24 contributes to an effect of causing a moving lens (which will be described later; see reference sign 32*b* in FIG. 4A) included in the optical system unit 32 to move in a direction along an optical axis O. The operation lever 24 is provided to be turnable in a direction of an arrow R around a shaft 24*x* as a turning center relative to an internal fixing portion (not illustrated) of the operation portion 10 as illustrated in FIG. 2. The operation lever 24 is configured such that if an operation end 24*a* of the operation lever 24 is caused to turn in the counterclockwise direction (in one direction along the arrow R) around the shaft 24*x*, for example, a traction wire 35*w* which is a traction member connected to an acting end 24*b* of the operation lever 24 can be pulled.

Also, the forceps port 12 provided at the operation portion 10 configures a proximal end-side opening portion of a treatment instrument channel (not illustrated in FIGS. 1 and 2; which will be described later) inserted and arranged between the operation portion 10 and a distal end-side opening part at the distal end portion 6 of the insertion portion 9. The endoscope system 1 is schematically configured as described above.

Next, the optical device according to the present embodiment and the internal structure of the distal end portion 6 of the endoscope 2 to which the optical device is applied will be described below in detail by using FIGS. 3, 4A, and the like in addition to FIG. 2.

Figure 3:
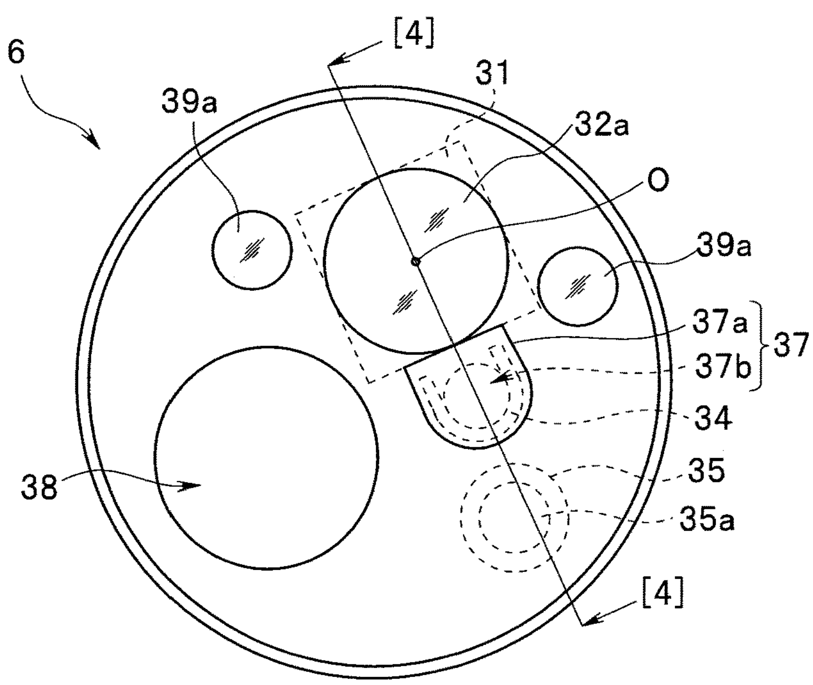
FIG. 3 is a conceptual diagram of a distal end portion of the endoscope in FIG. 1 seen from a front side.

FIG. 3 is a plan view illustrating a front surface of the distal end portion of the endoscope to which the optical device according to the present embodiment is applied. Note that FIG. 3 is a front view seen from a direction illustrated by an arrow [3] in FIG. 2. FIG. 4A is a conceptual diagram schematically illustrating the internal structure of the distal end portion of the endoscope to which the optical device according to the present embodiment is applied. Note that FIG. 4A is an enlarged view of a part illustrated by an arrow [4] in FIG. 2. Also, FIG. 4A is a diagram conceptually illustrating, in a simplified manner, member arrangement in a plane corresponding to a section along a line [4]-[4] in FIG. 3.

Figure 4A:
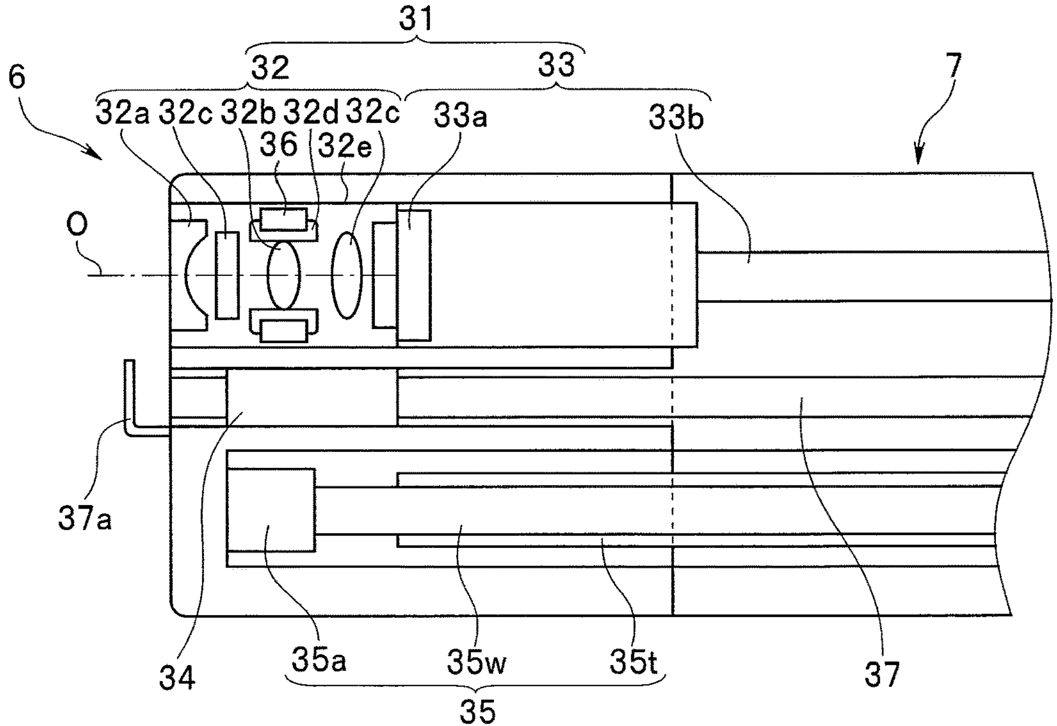
FIG. 4A is a conceptual diagram illustrating an internal configuration of the distal end portion of the endoscope in FIG. 1.

As illustrated in FIGS. 2 and 4A, a part of each of the drive unit, the cleaning unit, the illumination unit, and the treatment instrument channel is provided in addition to the observation unit 31 inside the distal end portion 6. Note that in FIGS. 2 and 4A, the illumination unit and the treatment instrument channel are not illustrated (details will be described later; see FIG. 3).

Among the components, the optical device according to the present embodiment is configured mainly of the observation unit 31 and the drive unit 35.

The observation unit 31 is configured of the optical system unit 32 and the image pickup unit 33.

The optical system unit 32 is configured of an image forming optical system that forms an optical image of an observation target on a predetermined image-forming plane, holding frame members (32*d*, 32*e*) that hold the image forming optical system, and the like.

Here, the image forming optical system includes a plurality of optical members (32*a*, 32*b*, 32*c*). In such a case, the plurality of optical members (32*a*, 32*b*, 32*c*) are arranged such that the respective optical axes are caused to coincide with an axis indicated by reference sign O and are aligned in a direction along the optical axis O.

Here, the optical member disposed on the side closest to the distal end and indicated by reference sign 32*a* is an observation window fixed to the front surface of the distal end portion 6.

Also, the optical member indicated by reference sign 32*b* from among the plurality of optical members is a moving lens that is subjected to an effect by the drive unit 35, which will be described later, and moves in the direction along the optical axis O. The moving lens 32*b* is held such that the moving lens 32*b* is movable in the direction along the optical axis O by the moving frame 32*d*. The moving frame 32*d* is provided with a magnet 36 that is a first magnetic body made of a ferromagnetic material. The magnet 36 (first magnetic body) functions as a configuration member that is subjected to an effect from the drive unit 35, which will be described later, and causes the moving frame 32*d* to move in the direction along the optical axis O.

Figure 4B:
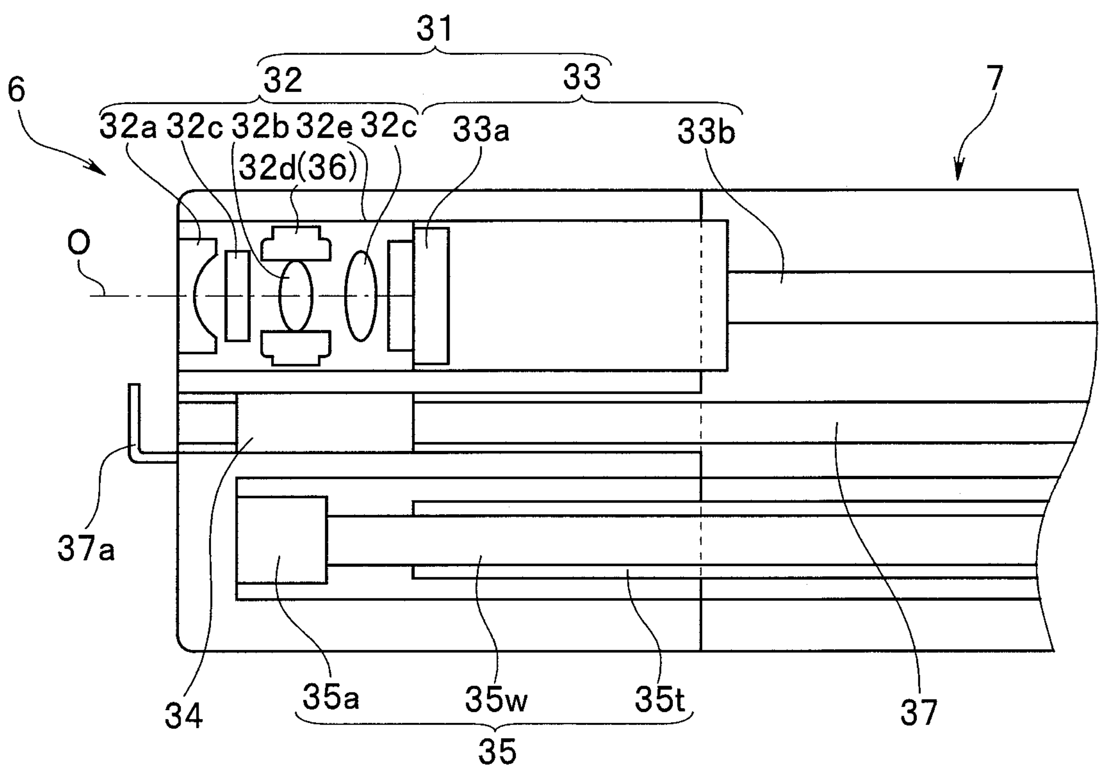
FIG. 4B is a conceptual diagram illustrating a modification of the internal configuration of the distal end portion of the endoscope in FIG. 1.

Note that although the magnet 36 as the first magnetic body is illustratively described as a member that is separated from the moving frame 32*d* in the present embodiment, the present invention is not limited to the form. Apart from the configuration example in the present embodiment, a configuration in which the moving frame 32*d* is formed of a ferromagnetic body, that is, a material with magnetism as illustrated in FIG. 4B, for example, may be employed. In the case of the configuration, the moving frame 32*d* itself functions as the first magnetic body. Note that FIG. 4B is a diagram illustrating a modification of the endoscope according to the present embodiment.

The plurality of optical members (two optical members in the example illustrated in FIGS. 2 and 4A) indicated by reference sign 32*c* from among the plurality of optical members are fixed lenses that are fixedly held by the holding frame 32*e* at a predetermined gap in the direction along the optical axis O. In such a case, the holding frame 32*e* holds the moving frame 32*d* such that the moving frame 32*d* is movable in the direction along the optical axis O and fixes the plurality of fixed lenses 32*c* at the respective predetermined positions. Therefore, the holding frame 32*e* is formed into a cylindrical shape formed of a non-magnetic material, for example. The moving frame 32*d* is held such that the moving frame 32*d* is movable along the optical axis O on an inner circumferential surface of the holding frame 32*e*.

The optical system unit 32 in the optical device according to the present embodiment with the configuration has a so-called multi-focal-point switching function by which it is possible to perform switching setting of a focal length by the moving lens 32*b* moving in the direction along the optical axis O and being arranged at a predetermined position.

The image pickup unit 33 is configured of an image pickup device 33*a*, an image pickup signal processing circuit (not illustrated), an image pickup signal cable 33*b*, and the like.

The image pickup device 33*a* is an image sensor that receives light of an optical image of an observation target formed by the optical system unit 32, performs predetermined photoelectric conversion processing, and generates an image signal. As the image pickup device 33*a*, a charge coupled device (CCD) image sensor or a complementary metal-oxide-semiconductor (CMOS) image sensor, for example, is applied.

The image pickup signal processing circuit is a signal processing circuit that performs predetermined signal processing on the image signal generated by the image pickup device 33*a* and generates image pickup data in a predetermined form.

The image pickup signal cable 33*b* is a signal line that transmits a signal outputted from the image pickup signal processing circuit to the video processor 4 and transmits a control signal from the video processor 4 to the image pickup unit 33. The image pickup signal cable 33*b* is inserted into the inside of the insertion portion 9, the operation portion 10, and the universal cord 17 from the image pickup unit 33 and is connected to the scope connector 18.

Then, the image pickup unit 33 is arranged behind the optical system unit 32 (on the side of the proximal end) inside the distal end portion 6. In such a case, the image pickup unit 33 is arranged such that the optical axis O of the optical system unit 32 and substantially the center point of the image pickup device 33*a* are caused to substantially coincide with each other. A light receiving surface of the image pickup device 33*a* of the image pickup unit 33 is arranged to be parallel with a plane that substantially perpendicularly intersects the optical axis O of the optical system unit 32.

The drive unit 35 is a configuration unit that causes a drive force for causing the moving frame 32*d* holding the moving lens 32*b* of the optical system unit 32 to move in the direction along the optical axis O to be generated. Therefore, the drive unit 35 is configured to include a drive magnet 35*a*, a traction wire 35*w*, a guide pipe 35*t*, and the like.

The drive magnet 35*a* is a configuration member that acts on the magnet 36 (first magnetic body) of the moving frame 32*d*. The drive magnet 35*a* is provided to be movable in a direction that is parallel with a long axis of the insertion portion 9 and is parallel with the optical axis O of the optical system unit 32 inside the distal end portion 6 by being subjected to an effect of the traction wire 35*w*.

In order to realize movement of the drive magnet 35*a* in the direction that is parallel with the optical axis O, a distal end of the traction wire 35*w* is coupled to the drive magnet 35*a*.

A proximal end of the traction wire 35*w* is coupled to the acting end 24*b* (see FIG. 2) of the operation lever 24. In other words, the traction wire 35*w* is a traction member arranged to be inserted into the inside of the insertion portion 9 between the inside (drive magnet 35*a*) of the distal end portion 6 and the inside (operation lever 24) of the operation portion 10. With the configuration, the traction wire 35*w* slides in the direction along the long axis of the insertion portion 9 in response to an operation (a turning operation in the direction of the arrow R in FIG. 2) of the operation lever 24. The drive magnet 35*a* is also configured to move in the same direction with the sliding of the traction wire 35*w* in the long axis direction of the insertion portion 9.

In the configuration, the sliding of the traction wire 35*w* in the long axis direction of the insertion portion 9 is guided by the guide pipe 35*t*.

The guide pipe 35*t* is a pipe-shaped member with an elongated shape having flexibility. The guide pipe 35*t* has a distal end fixed to the drive unit 35 and a proximal end fixed to a fixing portion 10*a* (see FIG. 2) inside the operation portion 10. The traction wire 35*w* is slidably inserted into the guide pipe 35*t*. Thus, the guide pipe 35*t* functions as a guide tube that allows the traction wire 35*w* to be inserted and guides a sliding direction of the traction wire 35*w*.

Note that respective movement amounts of the drive magnet 35*a* and the traction wire 35*w* in the long axis direction of the insertion portion 9 are defined by a movement amount (prescribed value) of the moving lens 32*b* (moving frame 32*d*) of the optical system unit 32 in the direction that is parallel with the optical axis O. In other words, the movement amount of the drive magnet 35*a* is set such that the drive magnet 35*a* can move by a movement amount that is substantially equivalent to the movement amount of the moving lens 32*b*, or the movement amount of the drive magnet 35*a* is set such that the drive magnet 35*a* can move by a movement amount that is larger than the movement amount of the moving lens 32*b*.

Incidentally, a part of each of the cleaning unit, the illumination unit, and the treatment instrument channel is provided in addition to the configuration members of the optical device (the observation unit 31 and the drive unit 35) according to the present embodiment inside the distal end portion 6 as described above.

Here, the cleaning unit is configured mainly of the cleaning solution supply pipe 37, a cleaning nozzle 37*a*, and the like. Among the components, the cleaning solution supply pipe 37 is inserted into the inside of the insertion portion 9, the operation portion 10, and the universal cord 17 and is connected to the scope connector 18. Furthermore, the scope connector 18 (see FIG. 1) is provided with a connecting pipe (not illustrated) to which a solution feeding tube extending from a cleaning solution tank through a solution feeding pump, which is not illustrated, is connected. Also, a terminal of the cleaning solution supply pipe 37 is connected to the connecting pipe. In other words, the cleaning solution supply pipe 37 configures a conduit line that is inserted from the cleaning solution tank to the distal end portion 6 for supplying a cleaning solution. Note that the configuration itself of the cleaning solution supply pipe 37 is the same as a configuration in a typical form that is applied to the conventional endoscope. Therefore, detailed description of the configuration will be omitted.

A part of a distal end of the cleaning solution supply pipe 37 is inserted into and arranged inside the distal end portion 6. Also, a distal most end part of the cleaning solution supply pipe 37 opens in the front surface of the distal end portion 6. In such a case, the front surface opening of the cleaning solution supply pipe 37 will be referred to as a solution supply pipe opening 37*b* (see FIG. 3).

Note that the distal end part of the cleaning solution supply pipe 37 is arranged in a region sandwiched between the observation unit 31 and the drive unit 35 inside the distal end portion 6 as illustrated in FIGS. 3 and 4A. Also, a yoke 34 that is a second magnetic body is provided in the form in which the yoke 34 surrounds an outer surface of the cleaning solution supply pipe 37, in a predetermined region at the distal end part of the cleaning solution supply pipe 37.

The yoke 34 that is the second magnetic body is a magnetic body that is a so-called yoke or the like that plays a role in guiding a magnetic flux (magnetic force) of the drive magnet 35*a* to the magnet 36 of the moving frame 32*d*. Therefore, the yoke 34 that is the second magnetic body serves as a part of main components of the optical device according to the present embodiment.

Figure 5:
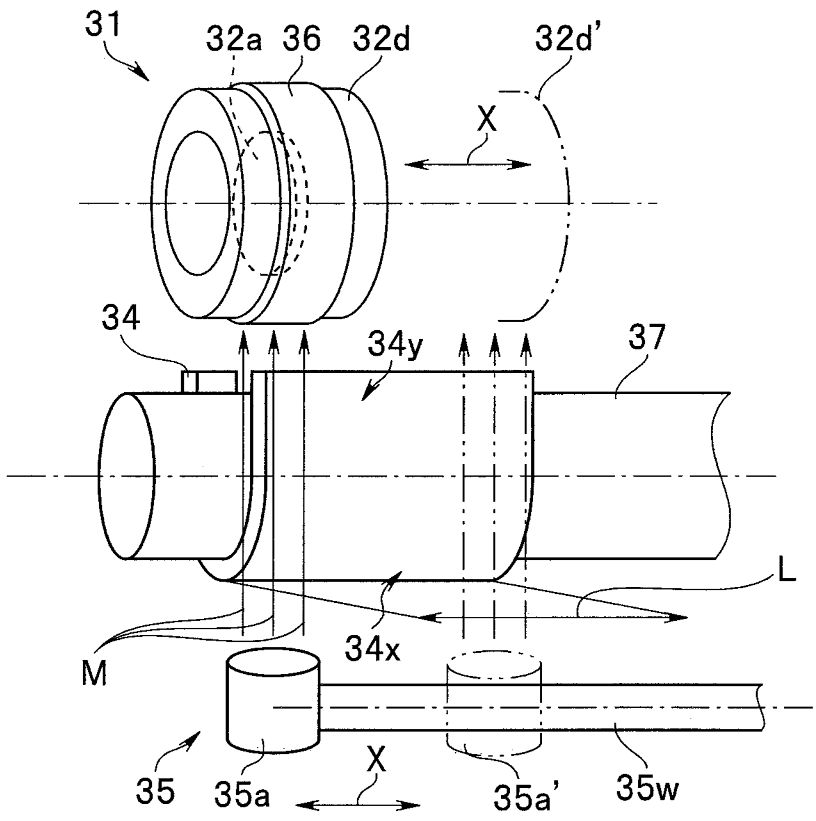
FIG. 5 is a conceptual diagram illustrating an arrangement example of a second magnetic body (yoke) in the optical device according to the embodiment of the present invention.
Figure 6:
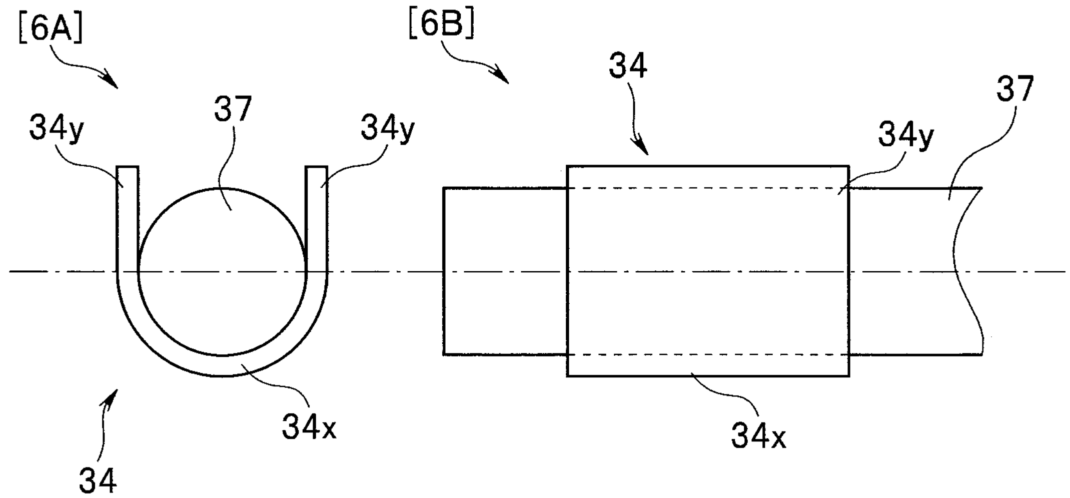
FIG. 6 is a conceptual diagram illustrating an example of a shape of the second magnetic body (yoke) in FIG. 5.

Here, FIGS. 5 and 6 are configuration diagrams illustrating an example of specific arrangement and shape of the yoke 34 that is the second magnetic body. Out of the drawings, FIG. 5 is a conceptual diagram illustrating an arrangement relationship among the yoke 34 arranged in the cleaning solution supply pipe 37, the moving frame 32*d*, and the drive magnet 35*a*. FIG. 6 is a conceptual diagram illustrating arrangement of the yoke 34 relative to the cleaning solution supply pipe 37 and the shape of the yoke 34. Note that in FIG. 6, reference sign [6A] illustrates a front shape of the yoke 34, and reference sign [6B] in the drawing illustrates a side shape of the yoke 34.

As illustrated in FIG. 5, the yoke 34 is arranged in a region between the moving frame 32*d* of the observation unit 31 and the drive magnet 35*a* of the drive unit 35 inside the distal end portion 6. Also, a length L (see FIG. 5) of the yoke 34 in the long axis direction is set to be a length that is substantially equivalent to a moving distance by which the moving frame 32*d* and the drive magnet 35*a* move in the long axis direction. Note that in FIG. 5, an arrow X indicates the moving direction of the moving frame 32*d* and the drive magnet 35*a*.

Here, reference sign 32*d*' indicated by a two-dotted dashed line in FIG. 5 indicates a moving end of the moving frame 32*d* on the side of the proximal end. Also, the moving frame 32*d* illustrated by a solid line in FIG. 5 indicates a moving end on the side of the distal end. Therefore, the moving distance of the moving frame 32*d* is a distance between a position indicated by the reference sign 32*d* and a position indicated by the reference sign 32*d*' indicated by the two-dotted dashed line in FIG. 5.

Similarly, reference sign 35*a*' indicated by a two-dotted dashed line in FIG. 5 indicates a moving end of the drive magnet 35*a* on the side of the proximal end. Also, the drive magnet 35*a* illustrated by a solid line in FIG. 5 indicates the moving end on the side of the distal end. Therefore, the moving distance of the drive magnet 35*a* is a distance between a position indicated by the reference sign 35*a* and a position indicated by the reference sign 35*a*' indicated by the two-dotted dashed line in FIG. 5.

Also, the yoke 34 is formed to have an open magnetic path structure in which one end portion is magnetically opened. Specifically, the yoke 34 is formed to have a substantially U shape when seen from the front as illustrated in FIG. 6 (see FIG. 3 as well), for example.

In such a case, the yoke 34 is arranged such that a bottom surface portion 34*x* of the substantially U shape faces the drive magnet 35*a* as illustrated in FIGS. 5 and 6. Also, two arm portions 34*y* of the substantially U shape serving as open ends are arranged to be directed to the magnet 36 (first magnetic body) of the moving frame 32*d*. In other words, the respective distal ends of the two arm portions 34*y* of the yoke 34 are arranged to be caused to face the magnet 36 (first magnetic body) of the moving frame 32*d*.

Note that when each member is arranged in the configuration, that is, when the drive magnet 35*a* and the magnet 36 are arranged with the yoke 34 sandwiched between the drive magnet 35*a* and the magnet 36, each member is arranged with orientations of magnetic fields (orientations indicated by N poles) matched.

By adopting the configuration, the magnetic flux (magnetic force) of the drive magnet 35*a* is constantly transmitted (guided) to the magnet 36 by the yoke 34 being arranged between the drive magnet 35*a* and the magnet 36 even when a state in which the magnetic flux (magnetic force) of the drive magnet 35*a* is not transmitted (guided) directly to the magnet 36 of the moving frame 32*d* is achieved due to separation of the region between the drive magnet 35*a* and the magnet 36 of the moving frame 32*d*. In other words, a line of magnetic force M from the drive magnet 35*a* is guided to the magnet 36 through the yoke 34 and can form a magnetic field as illustrated in FIG. 5. Therefore, it is thus possible to constantly cause the moving frame 32*d* to move in the same direction by causing the drive magnet 35*a* to move in the long axis direction. Also, it is possible to reliably cause the moving frame 32*d* to stop (be fixed) at a corresponding predetermined position when the drive magnet 35*a* is caused to stop (be fixed) at a predetermined position.

On the other hand, the cleaning nozzle 37*a* is provided at a position in the front surface of the distal end portion 6 facing the solution supply pipe opening 37*b* of the cleaning solution supply pipe 37. The cleaning nozzle 37*a* is provided at the front surface of the distal end portion 6 rather than the inside of the distal end portion 6. The cleaning nozzle 37*a* is provided to spray, toward the front surface of the observation window 32*a*, the cleaning solution that is supplied from the cleaning solution tank, which is not illustrated, through the cleaning solution supply pipe 37 to the distal end portion 6 of the endoscope 2 and is ejected forward from the solution supply pipe opening 37*b* and clean the front surface of the observation window 32*a*. The shape and the configuration of the cleaning nozzle 37*a* itself are the same as the shape and the configuration in a typical form applied to the conventional endoscope. Therefore, detailed description of the shape and the configuration will be omitted.

On the other hand, the illumination unit is an illumination device configured of an illumination member (not illustrated), such as an optical fiber bundle, that transmits illumination light supplied from the light source device 3 (see FIG. 1) to the distal end portion 6 of the endoscope 2, an illumination window 39*a* (see FIG. 3) that is an illumination lens to define a radiation range in which a light flux emitted from a distal end of the illumination member for radiation is caused to be transmitted and radiate a predetermined range in front of the distal end portion 6 of the endoscope 2, and the like. Therefore, the illumination member (not illustrated) such as an optical fiber bundle is inserted into the inside of the insertion portion 9, the operation portion 10, and the universal cord 17 from the distal end portion 6 to the scope connector 18. Note that the illumination unit is not limited to the form. For example, there is a form in which the illumination unit is configured by providing an illumination element such as an LED inside the distal end portion 6 as another form of the illumination unit. The illumination unit in the form is the same as an illumination unit in a typical form that is applied to the conventional endoscope. Therefore, detailed description of the illumination unit will be omitted.

The treatment instrument channel is a pipe-shaped member that is inserted and arranged between the operation portion 10 and the distal end portion 6 of the insertion portion 9. A proximal end-side opening portion of the treatment instrument channel is the forceps port 12, and the distal end portion 6 is provided with a distal end-side opening portion 38 (see FIG. 3). In this manner, the treatment instrument (not illustrated) inserted from the forceps port 12 on the side of the operation portion 10 can be inserted into the inside of the treatment instrument channel and can be caused to project from the distal end-side opening portion 38 toward the front side of the distal end portion 6. A configuration of the treatment instrument channel itself is the same as the configuration in the typical form that is applied to the conventional endoscope. Therefore, detailed description of the configuration will be omitted. The configuration of the optical device according to the present embodiment has been described hitherto.

Figure 7:
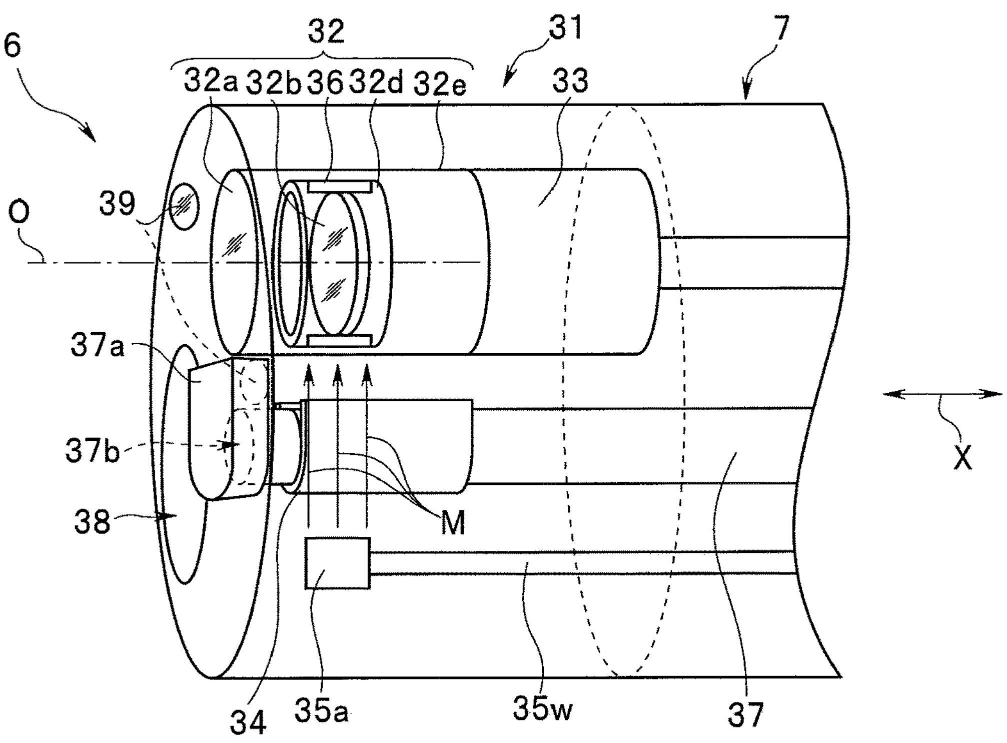
FIG. 7 is a conceptual diagram illustrating the internal configuration of the distal end portion of the endoscope in FIG. 1 and explaining an effect when a moving lens and a drive magnet move in an optical axis direction (a state where the moving lens and the drive magnet are arranged in a first position)
Figure 8:
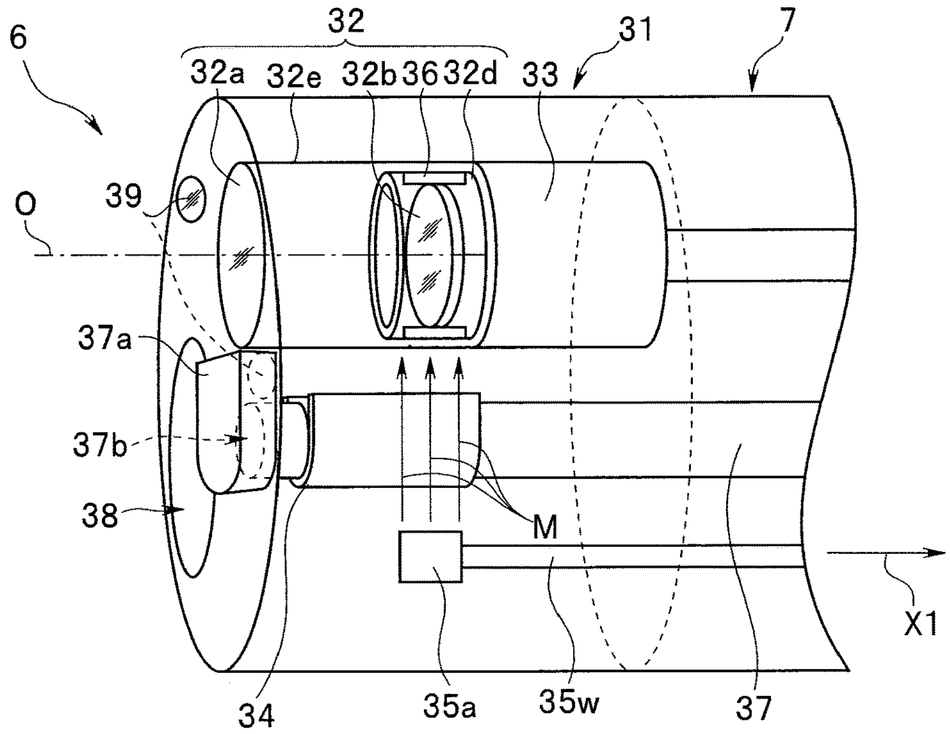
FIG. 8 is a conceptual diagram illustrating a state where the moving lens and the drive magnet have moved in the optical axis direction from the state in FIG. 7 and have moved to a second position.

Next, effects of the optical device according to the present embodiment will be briefly described below by using FIGS. 7 and 8. FIGS. 7 and 8 are conceptual diagrams conceptually illustrating an internal configuration of the distal end portion of the endoscope to which the optical device according to the present embodiment is applied and explaining effects when a focal length is switched by causing the moving lens and the drive magnet to move in the optical axis direction. Note that in order to avoid the drawings becoming complicated. FIGS. 7 and 8 are illustrated with some of components that are not needed for explanation omitted.

FIGS. 7 and 8 illustrate two aspects in a case where the drive unit and the moving lens have moved in the optical axis direction in the optical device according to the present embodiment, respectively. In other words, FIG. 7 illustrates a state in which the moving lens and the drive magnet are arranged at a first position that is closest to the distal end. FIG. 8 illustrates a state in which the moving lens and the drive magnet are arranged at a second position that is closest to the proximal end.

The optical device according to the present embodiment has a function by which it is possible to switch the focal length of the optical system unit 32 by causing the moving frame **32*d* holding the moving lens 32*b* to move in the direction along the optical axis O by using the drive unit 35** and to optically enlarge and observe an optical image of an observation target, for example.

An optical device in which the optical system unit 32 in the optical device according to the present embodiment is configured to be able to cause the moving frame **32*d* holding the moving lens 32*b* to move in the optical axis direction by the drive unit 35** and set two different focal lengths will be illustratively described.

As described above, in the optical device according to the present embodiment, the moving lens **32*b* held by the moving frame 32*d* is caused to move in the same direction (the direction along the optical axis O) by a drive force which is generated by the drive magnet 35*a* of the drive unit 35 moving in the direction along the optical axis O acting on the magnet 36 (first magnetic body) included in the moving frame 32*d***.

Therefore, the configuration members moving by the effect of the drive magnet **35*a* of the drive unit 35 in the optical device are the moving frame 32*d* including the magnet 36 and the moving lens 32*b*** in practice. However, the following wording will be used in the following description as a measure for avoiding the wording becoming complicated.

For example, when a configuration member moving by the drive unit 35 will be referred to, the configuration member will be simply referred to as the "moving lens **32*b*". In other words, the wording such as "the moving lens 32*b* moves" in the following description can be replaced as wording such as "the moving lens 32*b* held by the moving frame 32*d* including the magnet 36 moves in the direction along the optical axis O" or "the moving lens 32*b* held by the moving frame 32*d* also moves in the same direction at the same time (together) with the movement of the moving frame 32*d* including the magnet 36** in the optical axis direction".

As described above, FIG. 7 illustrates the state in which the moving lens **32*b* and the drive magnet 35*a* are arranged at the first position that is the closest to the distal end. When the moving lens 32*b* and the drive magnet 35*a* are arranged at the first position, the optical system unit 32 is set to have a first focal length out of two focal lengths that can be set. Note that as described above, the moving lens 32*b* and the drive magnet 35*a* of the drive unit 35 are configured to be movable in the direction along the arrow X illustrated in FIG. 7. Here, the arrow X direction is a direction that is parallel with the optical axis O. At the same time, the arrow X direction is a traction direction of the drive magnet 35*a* of the drive unit 35 and the traction wire 35*w***.

In the state illustrated in FIG. 7, the drive magnet **35*a* is arranged at the first position that is closest to the distal end. In the state, the line of magnetic force M from the drive magnet 35*a* is guided through the yoke 34 to the magnet 36 of the moving frame 32*d*. Thus, a magnetic force is generated among the drive magnet 35*a*, the yoke 34, and the magnet 36. When the drive magnet 35*a* moves with the magnetic force in the direction that is parallel with the optical axis O (the traction direction indicated by the arrow X), the moving lens 32*b* held by the moving frame 32*d* including the magnet 36** also moves in the same direction in conjunction with the movement.

Also, when the drive magnet **35*a* is at the first position, the moving lens 32*b* is also arranged at the first position. In the instance, the drive magnet 35*a* is in a stopping state at the first position. Thus, the moving lens 32*b* is in a stopping state at the corresponding first position due to an influence of the magnetic force of the drive magnet 35*a*. The stopping state of the moving lens 32*b* is maintained while the drive magnet 35*a*** is stopped.

Next, once a predetermined operation on the operation lever 24 is performed and the traction wire **35*w* of the drive unit 35 is pulled in a predetermined traction direction (an arrow X1 direction in FIG. 8) in the state illustrated in FIG. 7, the drive magnet 35*a* also moves in the same direction (the arrow X1 direction). Then, the drive magnet 35*a* moves to the position illustrated in FIG. 8**.

As described above, FIG. 8 illustrates the state in which the moving lens **32*b* and the drive magnet 35*a* are arranged at the second position that is the closest to the proximal end. Once the drive magnet 35*a* moves from the first position in FIG. 7 to the second position in FIG. 8, the moving lens 32*b* also moves from the first position in FIG. 7 to the second position in FIG. 8**.

Once the movement of the drive magnet **35*a* is stopped at the second position illustrated in FIG. 8, then the moving lens 32*b* also stops at the second position in FIG. 8. The stopping state of the moving lens 32*b* is maintained while the drive magnet 35*a* is stopped. Thus, once the moving lens 32*b* is arranged at the second position in FIG. 8, the optical system unit 32** is set to have the second focal length out of the two focal lengths that can be set.

On the other hand, it is possible to perform switching setting of the focal length by using substantially the same effect in a case of transition from the state in FIG. 8 to the state in FIG. 7 as well.

Thus, the moving frame **32*d* holding the moving lens 32*b* moves between the first position illustrated in FIG. 7 and the second position illustrated in FIG. 8 in the optical device according to the present embodiment. When the drive magnet 35*a* is brought into the stopping state at each of the first position illustrated in FIG. 7 and the second position illustrated in FIG. 8, the stopping state of the moving frame 32***d* is fixed at each of the predetermined positions and the position is maintained until an operation of moving the drive magnet 35*a* is performed.

As described above, each of the observation window 32*a* of the observation unit 31, the cleaning nozzle 37*a*, the solution supply pipe opening 37*b* of the cleaning solution supply pipe 37, the distal end-side opening portion 38 of the treatment instrument channel, the illumination windows 39*a* (multiple) of the illumination units, and the like is arranged at the predetermined position as illustrated in FIG. 3 when seen from the front side of the distal end portion 6, in the endoscope 2 to which the optical device according to the embodiment is applied.

In such a case, the cleaning solution supply pipe 37 is arranged in the vicinity of the observation unit 31, the observation unit 31 and the drive unit 35 are configured as separated members at positions at which the observation unit 31 and the drive unit 35 substantially face each other with the cleaning solution supply pipe 37 sandwiched, and the observation unit 31 and the drive unit 35 are arranged at positions separated from each other, in the optical device according to the present embodiment. Also, the optical device is configured to be provided with the yoke 34 in the form in which the yoke 34 surrounds the outer surface of the cleaning solution supply pipe 37 arranged in the region between the moving frame 32*d* of the observation unit 31 and the drive magnet 35*a* of the drive unit 35.

According to the optical device in the present embodiment, the cleaning solution supply pipe 37 is arranged in the vicinity of the observation unit 31, and a function of cleaning the front surface of the observation window 32*a* is maintained, by employing the configuration. At the same time, the observation unit 31 (the moving frame 32*d* including the magnet 36) and the drive unit 35 (the drive magnet 35*a*) are separated configurations thereby to realize the arrangement in which the observation unit 31 and the drive unit 35 are separated. In such a case, the yoke 34 is arranged in the region between the observation unit 31 and the drive unit 35, and it is thus possible to reliably perform movement of the moving frame 32*d* in the direction along the optical axis O by the drive unit 35. At the same time, it is possible to reliably cause the moving frame 32*d* to stop at a desired predetermined position (a predetermined position at which the targeted focal length in the optical system unit 32 can be set) and to reliably maintain the stopping state of the moving frame 32*d*.

In other words, simplification of the structure is realized by including the observation unit 31 (the moving frame 32*d* including the magnet 36) and the drive unit 35 (the drive magnet 35*a*) as separated configurations, and in addition, an improvement in efficiency of assembly is also realized by simplifying the structure.

It is possible to reliably guide the magnetic force from the drive magnet 35*a* to the magnet 36 of the moving frame 32*d* through the yoke 34 by arranging the yoke 34 (second magnetic body) between the magnet 36 (first magnetic body) of the moving frame 32*d* and the drive magnet 35*a* of the drive unit 35. Therefore, it is possible to contribute to an improvement in degree of freedom in arranging the drive unit 35 relative to the observation unit 31 including the moving frame 32*d* of the optical system unit 32 and thus to contribute to size reduction and diameter reduction of the distal end portion 6 of the endoscope 2.

Also, the state in which the moving frame 32*d* holding the moving lens 32*b* is attracted to the side of the drive magnet 35*a* is constantly maintained by the magnetic force of the drive magnet 35*a* in the stopping state. Therefore, it is possible to precisely maintain optical performance of the optical system unit 32 without causing eccentricity (shift), inclination (tilt), and the like of the optical axis O of the moving lens 32*b*.

Furthermore, since the configuration using only the magnetic force generated between the magnet 36 (first magnetic body) included in the moving frame 32*d* and the drive magnet 35*a* as a drive force when the moving frame 32*d* moves and for maintaining the stopping state of the moving frame 32*d* at the predetermined stopping position is employed, it is possible to eliminate a need of power supply or the like.

Note that although the configuration in which the focal length is switched by causing the moving frame 32*d* holding the moving lens 32*b* to move in the direction along the optical axis O by using the drive unit 35 has been illustratively described in the aforementioned embodiment, the configuration of the present invention is not limited to the illustratively described configuration. For example, the configuration according to the present embodiment can be applied to the moving lens 32*b* for realizing a focal point adjustment function (focusing function) in exactly the same manner.

Incidentally, although the configuration example in which the cleaning solution supply pipe 37 is arranged in the region between the observation unit 31 and the drive unit 35 and the cleaning solution supply pipe 37 is provided with the yoke 34 that is the second magnetic body has been described in the aforementioned embodiment, the configuration of the present invention is not limited to the configuration example.

As configuration examples that are different from the configuration example of the embodiment, configurations as described below can be illustratively described.

Figure 9:
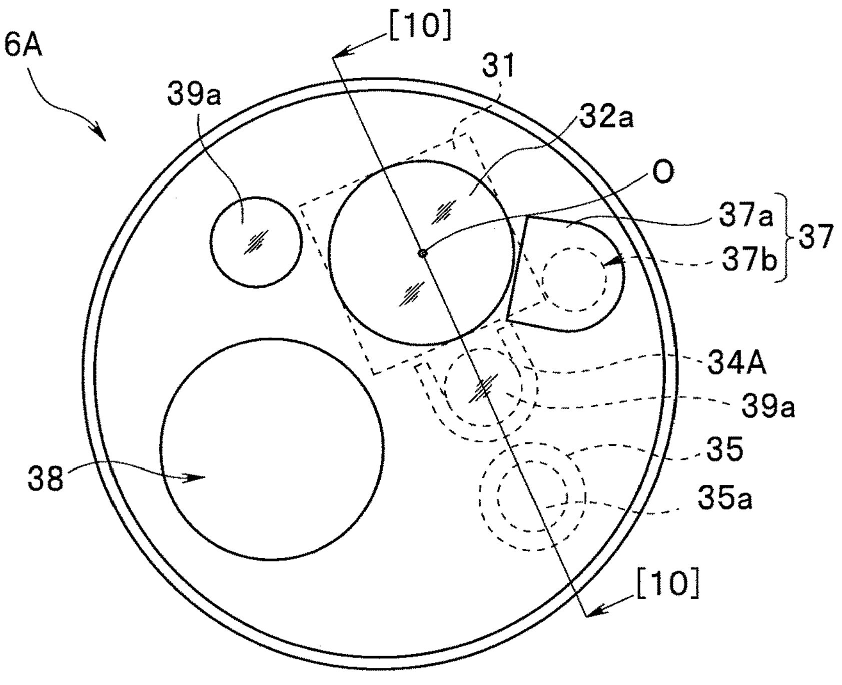
FIG. 9 is a conceptual diagram illustrating a different configuration example of the distal end portion of the endoscope to which the optical device according to the embodiment of the present invention is applied, in which the distal end portion is seen from the front side.
Figure 10:
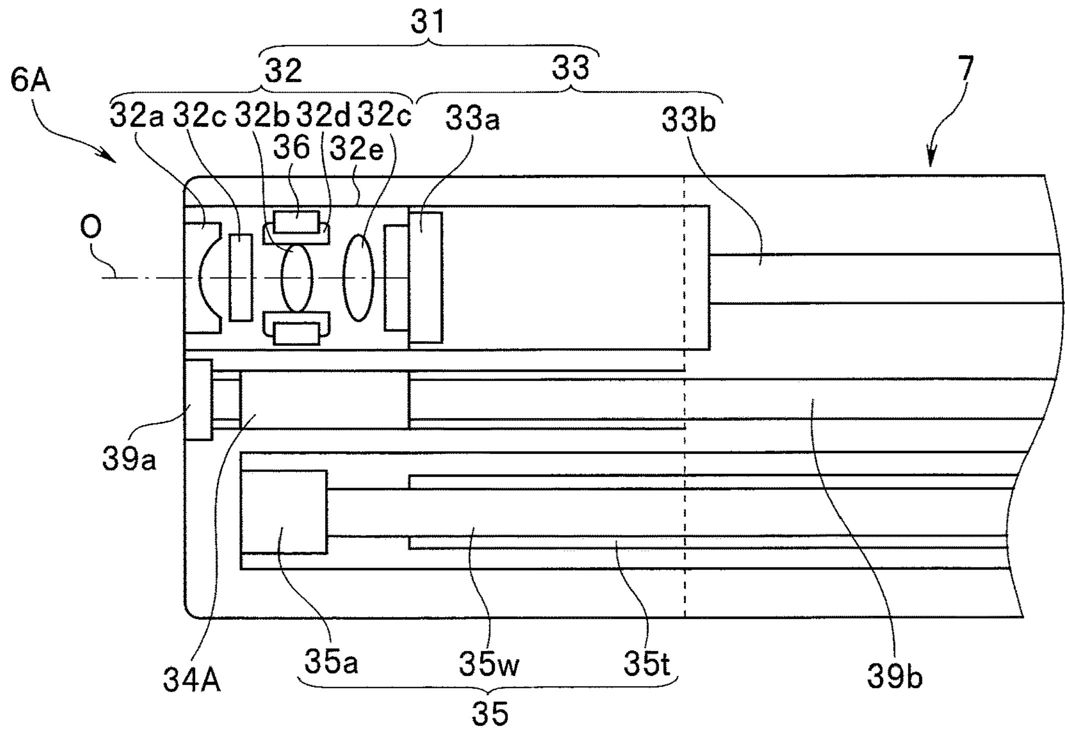
FIG. 10 is a conceptual diagram illustrating an internal configuration of the distal end portion of the endoscope in FIG. 9.

FIGS. 9 and 10 are diagrams illustrating a different configuration example of member arrangement inside a distal end portion in an endoscope to which an optical device according to the embodiment of the present invention is applied. Out of these drawings, FIG. 9 is a diagram conceptually illustrating member arrangement when the distal end portion is seen from the front side. FIG. 10 is a diagram conceptually illustrating, in a simplified manner, member arrangement in a plane corresponding to a section along a line [10]-[10] in FIG. 9.

As illustrated in FIGS. 9 and 10, an example in which one illumination unit (an illumination window 39*a* and an illumination member 39*b* such as an optical fiber bundle) among a plurality of illumination units is arranged in a region between an observation unit 31 and a drive unit 35 in a distal end portion 6A illustrated in the different configuration example is illustrated.

Also, in the different configuration example, a yoke 34A that is a second magnetic body is provided at a part of the illumination member 39*b* of the illumination unit. Here, the yoke 34A is provided in a predetermined region at a distal end part of the illumination member 39*b* in a form in which the yoke 34A surrounds an outer surface of the illumination member 39*b*. The other configurations are exactly the same as the configurations in the aforementioned embodiment.

In the different configuration example, it is also possible to obtain exactly the same effects as the effects obtained in the case in which the aforementioned configuration example in the first embodiment is adopted.

On the other hand, although the example in which the yokes 34 and 34A are formed into substantially U shapes as illustrated in FIGS. 3, 5 to 9, and the like has been described as an example of the shape of the yokes 34 and 34A that are second magnetic bodies in the aforementioned embodiment, the shape of the second magnetic body (yoke) is not limited to the illustratively described shape.

It is only necessary for the second magnetic body (yoke) applied to the optical device according to the present embodiment to be formed as an open magnetic path structure. Therefore, as a different example of the shape of the second magnetic body (yoke), a substantially channel shape as illustrated in FIGS. 11 and 12, for example, may be employed.

Figure 11:
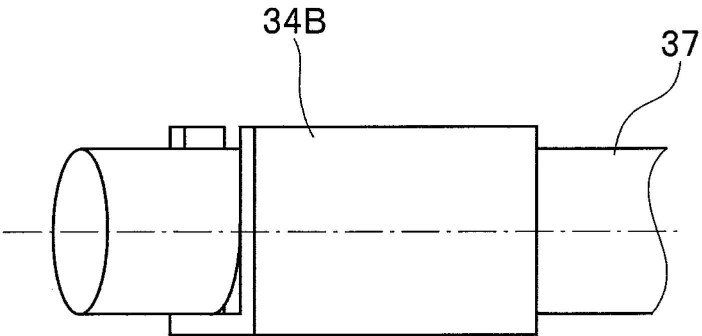
FIG. 11 is a conceptual diagram illustrating a different example of the shape of the second magnetic body (yoke) in the optical device according to the embodiment of the present invention and illustrating an arrangement example of the second magnetic body (yoke)
Figure 12:
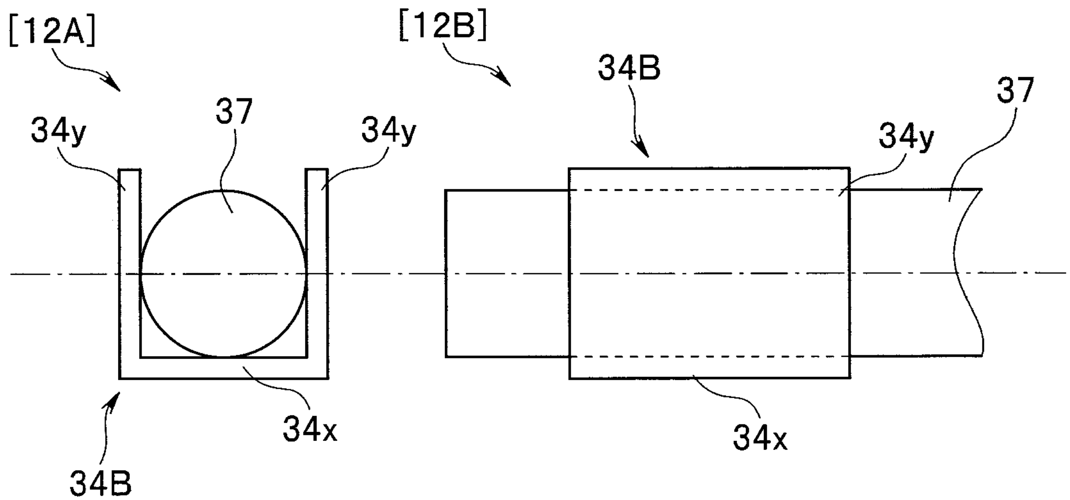
FIG. 12 is a conceptual diagram illustrating the shape of the second magnetic body (yoke) in FIG. 11.

FIGS. 11 and 12 are diagrams illustrating the different example of the shape of the second magnetic body (yoke). Out of these drawings, FIG. 11 is a perspective view illustrating an arrangement state of a yoke 34B that is a second magnetic body in the different example of the shape in the cleaning solution supply pipe 37. Also, FIG. 12 is a diagram conceptually illustrating arrangement of the yoke 34B that is the second magnetic body in the cleaning solution supply pipe 37 and the shape of the yoke 34B. Note that in FIG. 12, reference sign [12A] denotes a front shape of the yoke 34B that is the second magnetic body, and reference sign [12B] in the drawing denotes a side shape of the yoke 34B that is the second magnetic body. In FIGS. 11 and 12, the cleaning solution supply pipe 37 can be replaced with an illumination member. Even with the thus formed yoke 34B that is the second magnetic body, it is possible to obtain exactly the same configuration as the configuration in the aforementioned embodiment.

On the other hand, as a yet different example of the shape of the second magnetic body (yoke), the second magnetic body (yoke) may have a shape formed only by two arm portions 34*y* with bottom surface portion 34*x* of the yokes 34 and 34B illustratively described in FIGS. 6 and 12, for example, omitted.

In other words, although not illustrated in the drawings, second magnetic bodies (yokes) are formed into two I shapes in the different example of the shape. In such a case, the two yokes with the I shapes are arranged to sandwich and surround the cleaning solution supply pipe or the illumination member. The two yokes with the I shapes are arranged with each long axis direction directed to the first magnetic body of the moving frame. In other words, the two yokes with the I shapes are arranged with distal ends facing the first magnetic body. Furthermore, the two yokes with the I shapes may be arranged with the other ends facing the magnet of the drive unit. As described above, it is desirable that the first magnetic body, the second magnetic body, and the magnet be arranged to be aligned on substantially one straight line. However, the arrangement of the members is not necessarily arrangement on substantially one straight line, and it is only necessary for the magnetic force from the magnet to be guided by the second magnetic body and to be able to be efficiently transmitted to the first magnetic body in the arrangement.

The second magnetic body (yokes 34, 34A, 34B) illustratively described in the optical device according to the aforementioned embodiment is configured of one member having a length L (see FIG. 5) in the long axis direction. However, the configuration of the second magnetic body (yokes 34, 34A, 34B) is not limited to the aforementioned example. For example, various modifications as described below are conceivable.

Figure 13:
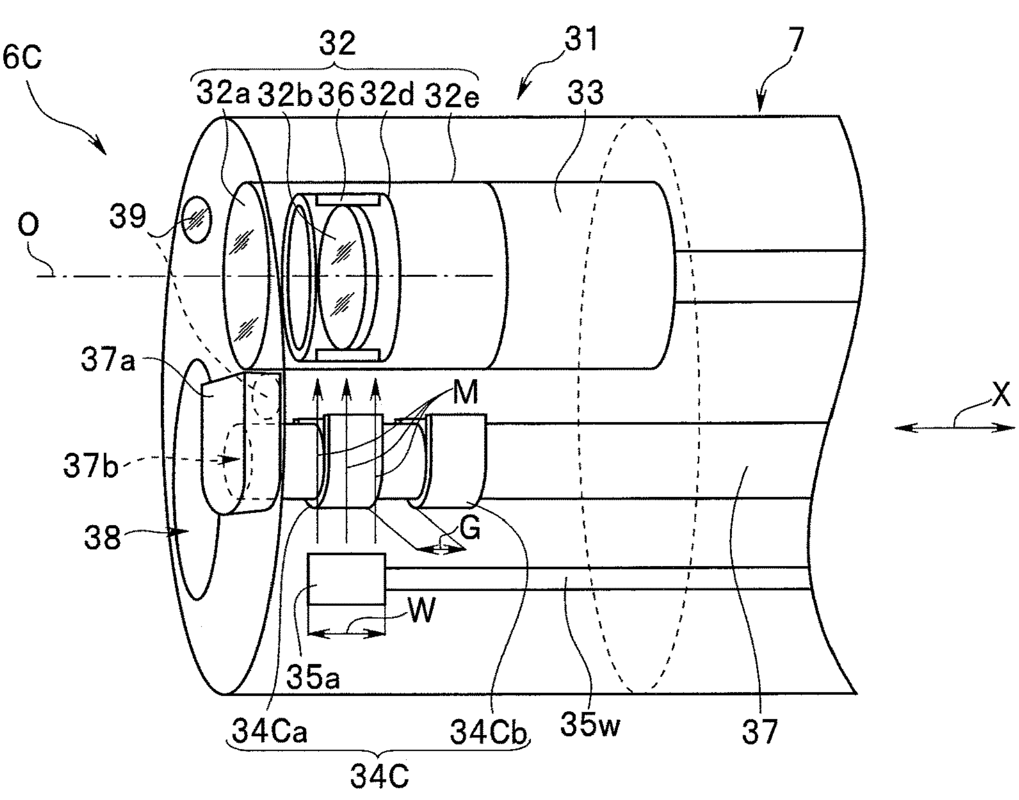
FIG. 13 is a conceptual diagram illustrating an internal configuration of a distal end portion of an endoscope to which an optical device according to a first modification of the embodiment of the present invention is applied and explaining an effect when a moving lens and a drive magnet move in an optical axis direction (a state where the moving lens and the drive magnet are arranged in the first position)
Figure 14:
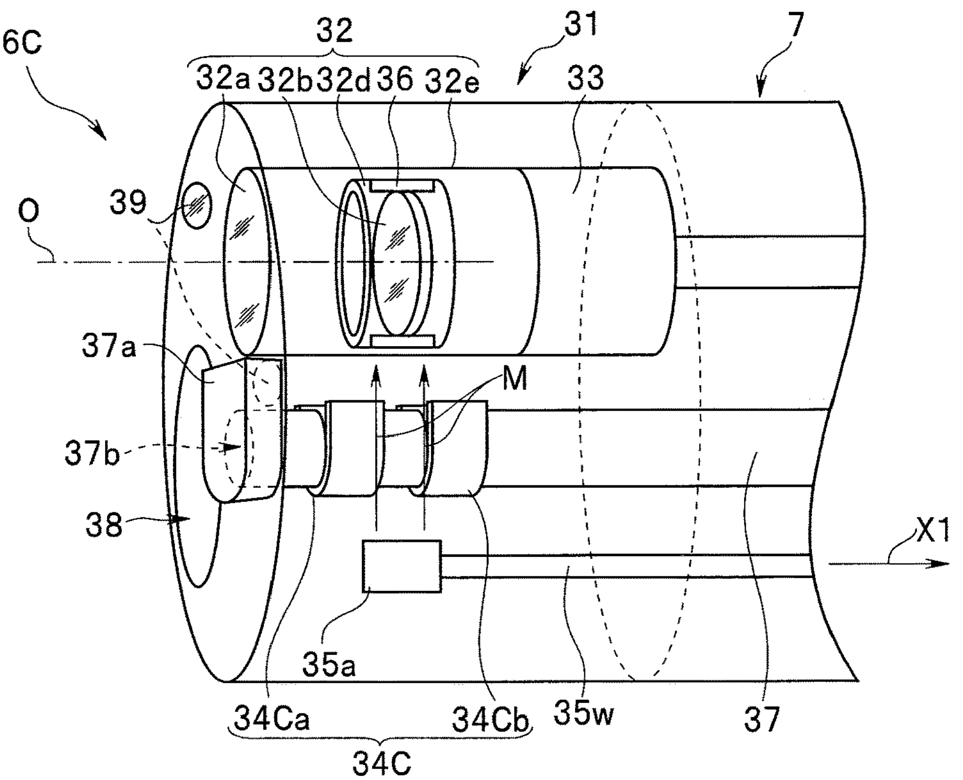
FIG. 14 is a conceptual diagram illustrating a state where the moving lens and the drive magnet have moved in the optical axis direction from the state in FIG. 13 and have been arranged at an intermediate position between the first position and the second position.
Figure 15:
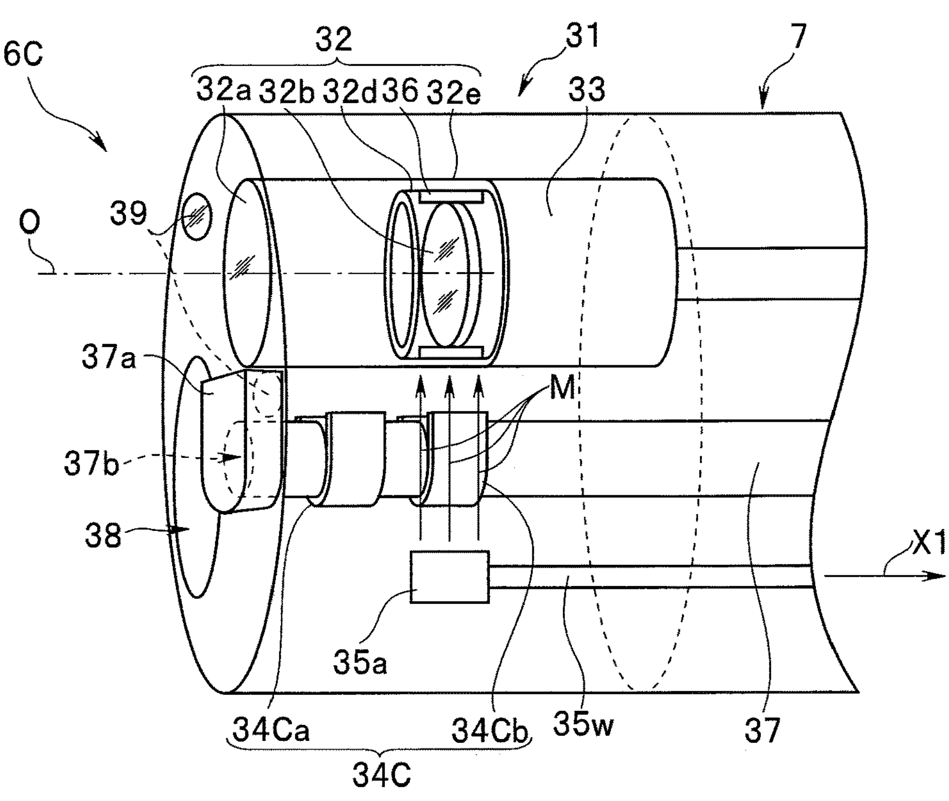
FIG. 15 is a conceptual diagram illustrating a state where the moving lens and the drive magnet have moved in the optical axis direction from the state in FIG. 14 and have been arranged in the second position that is closest to a proximal end.

Next, a first modification of the optical device according to the embodiment of the present invention will be described below. FIGS. 13 to 15 are conceptual diagrams conceptually illustrating an internal configuration of a distal end portion of an endoscope to which an optical device according to the first modification of the embodiment of the present invention is applied and explaining effects obtained when a focal length is switched by causing a moving lens and a drive magnet to move in an optical axis direction.

FIGS. 13 to 15 illustrate three aspects in a case in which a drive unit and the moving lens move in the optical axis direction in the optical device according to the first modification, respectively. In other words, FIG. 13 illustrates a state in which the moving lens and the drive magnet are arranged at a first position that is the closest to a distal end. FIG. 14 illustrates a state in which the moving lens and the drive magnet are arranged at an intermediate position between the first position and a second position. FIG. 15 illustrates a state in which the moving lens and the drive magnet are arranged at the second position that is the closest to a proximal end.

A basic configuration of the optical device according to the first modification of the embodiment of the present invention is substantially the same as the basic configuration in the aforementioned embodiment. In the optical device according to the first modification, only a configuration of a yoke 34C that is a second magnetic body is different from the configuration in the optical device according to the aforementioned embodiment. Therefore, the same configurations as the configurations in the optical device according to the aforementioned embodiment will be denoted by the same reference signs, detailed description of the same configurations will be omitted, and only different configurations will be described in detail, in the following description regarding the optical device according to the first modification.

As illustrated in FIGS. 13 to 15, the optical device according to the first modification is an optical device having a so-called multi-focal-point switching function by which it is possible to perform switching setting of a focal length by a moving lens 32*b* of an optical system unit 32 moving in the direction along the optical axis O and being arranged at a predetermined position inside a distal end portion 6C. Regarding the point, the optical device according to the first modification is the same as the optical device according to the aforementioned embodiment.

The yoke 34C that is a second magnetic body in the optical device according to the first modification is configured of a plurality of magnetic bodies. The yoke 34C is provided for each of a plurality of focal lengths that can be set by the optical system unit 32. Here, the optical device according to the first modification is illustratively described as a two-focal-point switching type optical device.

In other words, the yoke 34C includes two yokes, namely a first yoke 34Ca arranged at a position corresponding to the first position of the moving lens 32*b* and the drive magnet 35*a* and a second yoke 34Cb arranged at a position corresponding to the second position of the moving lens 32*b* and the drive magnet 35*a* inside the distal end portion 6C of the endoscope to which the optical device according to the first modification is applied. In other words, the two yokes (34Ca, 34Cb) are provided in the same number as the number of focal lengths that the optical system unit 32 can set.

Each of the first yoke 34Ca and the second yoke 34Cb is formed into a substantially U shape. Also, each of the yokes 34Ca and 34Cb is provided in a form in which each of the yokes 34Ca and 34Cb surrounds an outer surface of a cleaning solution supply pipe 37. The first yoke 34Ca and the second yoke 34Cb are fixed to be separated from each other at a predetermined gap G (see FIG. 13) in the axial direction at predetermined positions that are close to the distal end of the cleaning solution supply pipe 37. In the instance, each distal end of each arm portion of each of the yokes 34Ca and 34Cb is arranged to face the magnet 36 (first magnetic body) of the moving frame 32*d*. Also, the bottom surface portion of each of the yokes 34Ca and 34Cb is arranged to face the drive magnet 35*a*.

The gap G (see FIG. 13) between the first yoke 34Ca and the second yoke 34Cb is set to a predetermined gap in accordance with a size (a dimension W in the long axis direction) of the drive magnet 35*a*. For example, the gap G between the first yoke 34Ca and the second yoke 34Cb is set to be less than the dimension W of the drive magnet 35*a* in the long axis direction (W>G).

Thus, the line of magnetic force M from the drive magnet 35*a* is constantly guided to the magnet 36 and is not interrupted when the drive magnet 35*a* moves in the direction indicated by the arrow X between the first position that is the closest to the distal end and the second position that is the closest to the proximal end by setting the gap G between the first yoke 34Ca and the second yoke 34Cb. In other words, a configuration of maintaining a state in which the line of magnetic force M from the drive magnet 35*a* is constantly guided to the magnet 36 even when the drive magnet 35*a* is at the intermediate position between the position facing the first yoke 34Ca and the position facing the second yoke 34Cb (see FIG. 14) is employed. The other configurations are the same as the configurations in the aforementioned embodiment.

Effects of the optical device according to the first modification with the configuration are as illustrated in FIGS. 13 to 15. FIG. 13 illustrates the state in which the moving lens 32*b* and the drive magnet 35*a* are arranged at the first position that is the closest to the distal end. When the moving lens 32*b* and the drive magnet 35*a* are arranged at the first position, the optical system unit 32 are set to have a first focal length out of two focal lengths that can be set.

In the state illustrated in FIG. 13, the drive magnet 35*a* is arranged at the first position that is the closest to the distal end. In the state, the line of magnetic force M from the drive magnet 35*a* is guided to the magnet 36 of the moving frame 32*d* through the first yoke 34Ca A magnetic force is thus generated among the drive magnet 35*a*, the first yoke 34Ca, and the magnet 36. Once the drive magnet 35*a* moves in the direction that is parallel with the optical axis O (the traction direction indicated by the arrow X) with the magnetic force, the moving lens 32*b* held by the moving frame 32*d* including the magnet 36 also moves in the same direction in conjunction with the movement.

Also, when the drive magnet 35*a* is at the first position, the moving lens 32*b* is also arranged at the first position. In the instance, the drive magnet 35*a* is in the stopping state at the first position. The moving lens 32*b* is thus in the stopping state at the corresponding first position due to an influence of the magnetic force of the drive magnet 35*a*. The stopping state of the moving lens 32*b* is maintained while the drive magnet 35*a* is stopped.

Next, once a predetermined operation on the operation lever 24 is performed in the state illustrated in FIG. 13 and the traction wire 35*w* of the drive unit 35 is pulled in the predetermined traction direction (the arrow X1 direction in FIG. 14), the drive magnet 35*a* also moves in the same direction (the arrow X1 direction). Then, the drive magnet 35*a* moves to the position illustrated in FIG. 14.

As described above. FIG. 14 illustrates the state in which the moving lens 32*b* and the drive magnet 35*a* are arranged at the intermediate position between the first position and the second position. Once the drive magnet 35*a* moves from the first position in FIG. 13 to the intermediate position in FIG. 14, the moving lens 32*b* also moves from the first position in FIG. 13 to the intermediate position in FIG. 14.

In the instance, a part of the line of magnetic force M from the drive magnet 35*a* is guided through the first yoke 34Ca, another part of the line of magnetic force M is guided through the second yoke 34Cb, and both the parts are guided to the magnet 36 of the moving frame 32*d*. In other words, when the drive magnet 35*a* moves from the first position in FIG. 13 to the second position in FIG. 15 via the intermediate position illustrated in FIG. 14, the line of magnetic force M from the drive magnet 35*a* is constantly continuously guided to the magnet 36 and is not interrupted. Therefore, when the drive magnet 35*a* moves in the arrow X1 direction, the moving frame 32*d* holding the moving lens 32*b* can also continuously move in the same direction in conjunction with the movement.

Next, if the drive magnet 35*a* further continues the movement in the arrow X1 direction via the state in FIG. 14, the state in FIG. 15 is eventually achieved. FIG. 15 illustrates the state in which the moving lens 32*b* and the drive magnet 35*a* are arranged at the second position that is the closest to the proximal end.

Once the movement of the drive magnet 35*a* is stopped at the second position illustrated in FIG. 15, the moving lens 32*b* also stops at the second position in FIG. 15. Then, the stopping state of the moving lens 32*b* is maintained while the drive magnet 35*a* is stopped. Thus, once the moving lens 32*b* is arranged at the second position in FIG. 15, the optical system unit 32 is set to have the second focal length out of the two focal lengths that can be set. Note that it is possible to perform switching setting of the focal length by substantially the same effect in a case of transition from the state in FIG. 15 to the state in FIG. 13 via the state in FIG. 14.

As described above, the moving frame 32*d* holding the moving lens 32*b* moves between the first position illustrated in FIG. 13 and the second position illustrated in FIG. 15 in the optical device according to the first modification. When the drive magnet 35*a* is brought into the stopping state at each position out of the first position illustrated in FIG. 13 and the second position illustrated in FIG. 15, the moving frame 32*d* is fixed in the stopping state at each predetermined position, and the position is maintained until an operation of moving the drive magnet 35*a* is performed.

Furthermore, the optical device according to the first modification is configured to be provided with the first yoke 34Ca corresponding to the first position of the moving lens 32*b* and the drive magnet 35*a* and the second yoke 34Cb corresponding to the second position of the moving lens 32*b* and the drive magnet 35*a*. According to the configuration, the magnetic force of the drive magnet 35*a* can be more efficiently guided to the moving frame 32*d* at each position out of the first position and the second position of the drive magnet 35*a*. It is thus possible to reliably maintain the stopping state of the moving frame 32*d* at each position out of the first position and the second position. In other words, it is possible to easily and reliably define the setting of the stopping position of the moving frame 32*d* by appropriately setting the arrangement of the plurality of yokes.

Figure 16:
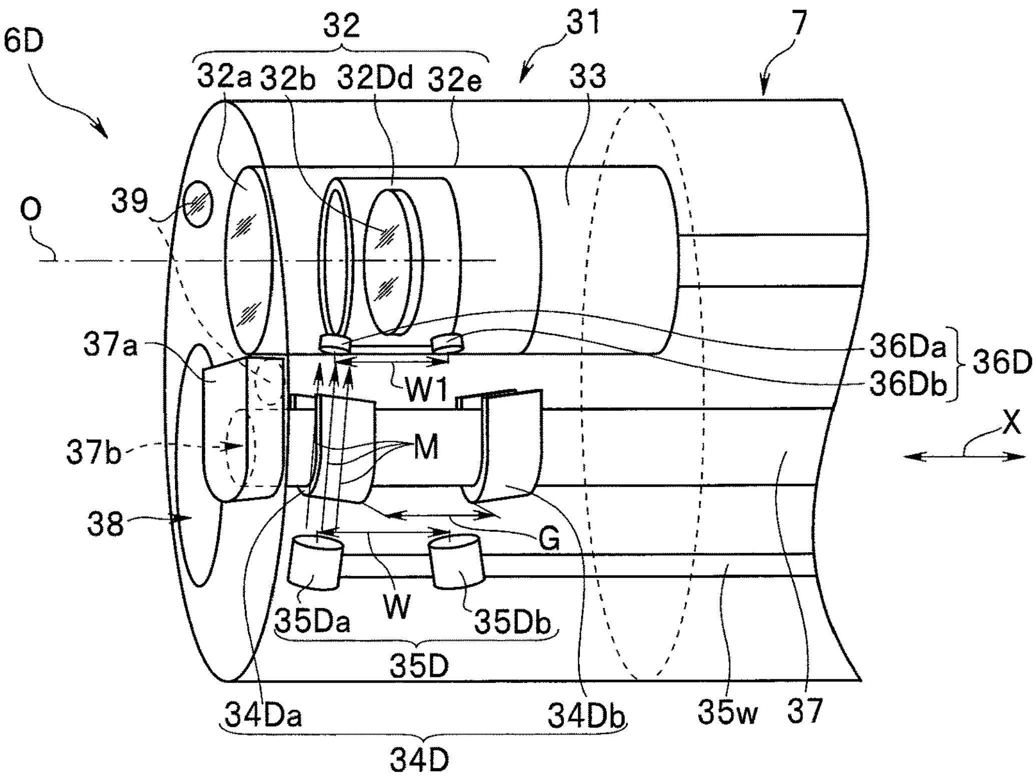
FIG. 16 is a conceptual diagram illustrating an internal configuration of a distal end portion of an endoscope to which an optical device according to a second modification of the embodiment of the present invention is applied and explaining an effect when a moving lens and a drive magnet move in an optical axis direction (a state where the moving lens and the drive magnet are arranged in the first position)
Figure 17:
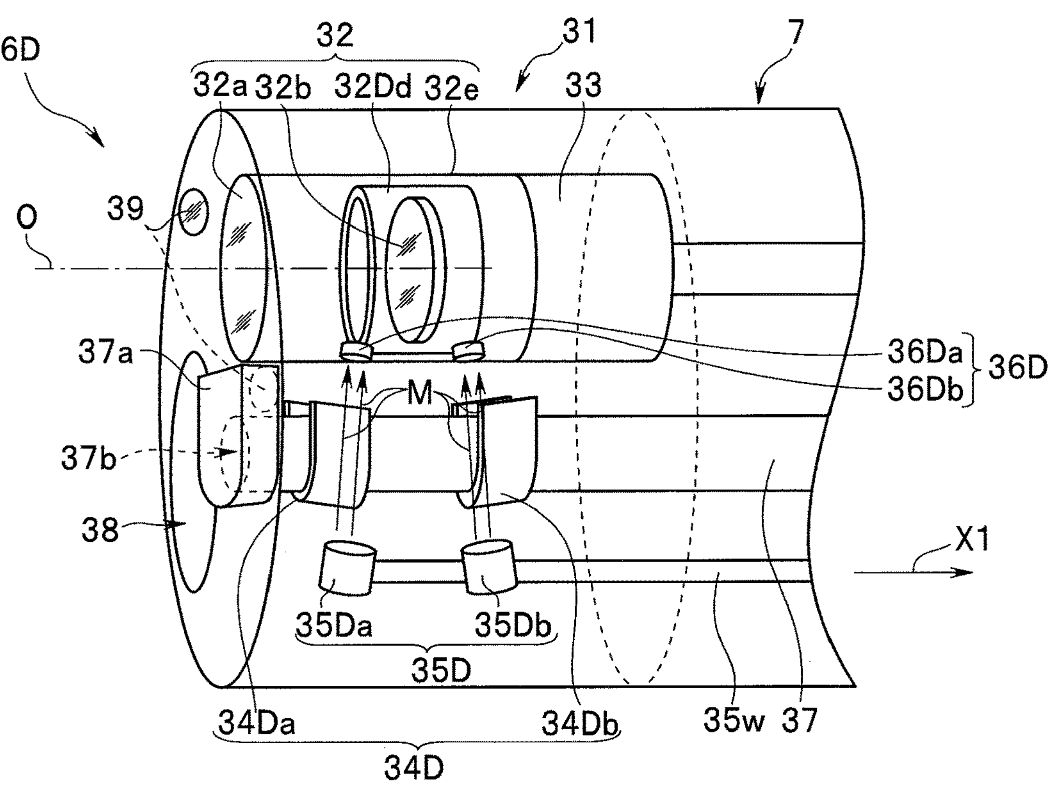
FIG. 17 is a conceptual diagram illustrating a state where the moving lens and the drive magnet have moved in the optical axis direction from the state in FIG. 16 and have been arranged at the intermediate position between the first position and the second position.
Figure 18:
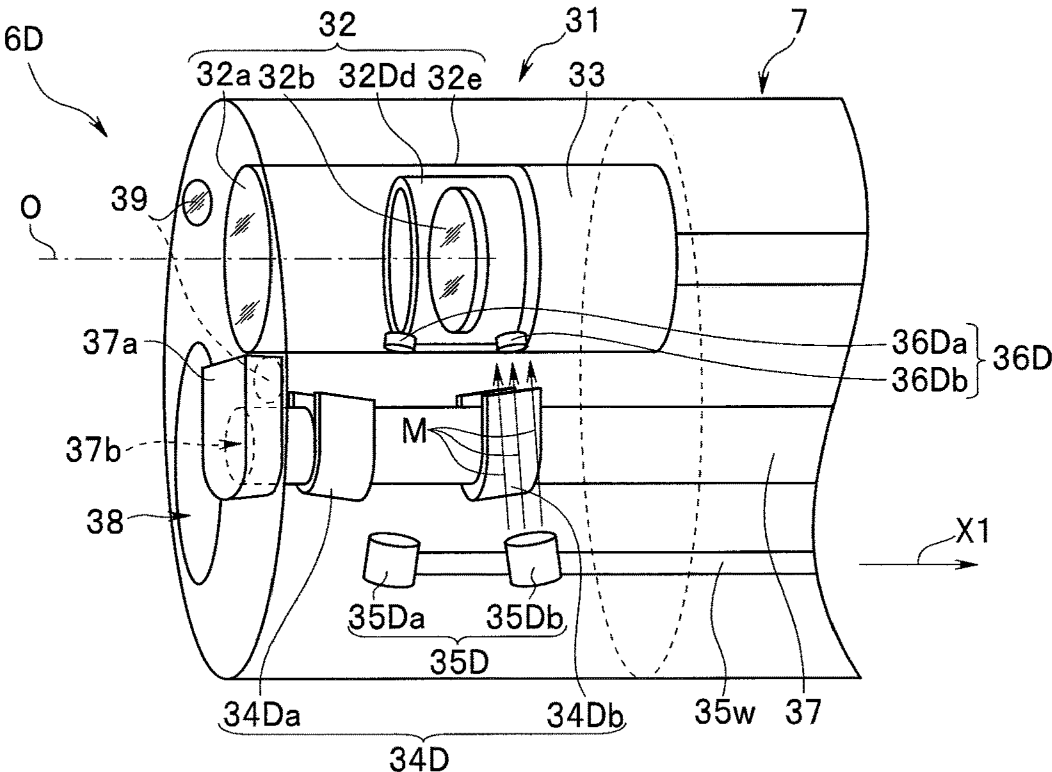
FIG. 18 is a conceptual diagram illustrating a state where the moving lens and the drive magnet have moved in the optical axis direction from the state in FIG. 17 and have been arranged in the second position that is closest to the proximal end.

Next, a second modification of the optical device according to the embodiment of the present invention will be described below. FIGS. 16 to 18 are conceptual diagrams conceptually illustrating an internal configuration of a distal end portion of an endoscope to which the optical device according to the second modification of the embodiment of the present invention is applied and explaining an effect when a moving lens and a drive magnet are caused to move in an optical axis direction and a focal length is switched.

FIGS. 16 to 18 are diagrams that are equivalent to FIGS. 13 to 15 illustrating the aforementioned first modification. In other words, FIGS. 16 to 18 illustrate three aspects in a case in which the drive unit and the moving lens move in the optical axis direction in the optical device according to the second modification. Among the drawings, FIG. 16 illustrates a state in which the moving lens and the drive magnet are arranged at a first position that is the closest to a distal end. FIG. 17 illustrates a state in which the moving lens and the drive magnet are arranged at an intermediate position between the first position and a second position. FIG. 18 illustrates a state in which the moving lens and the drive magnet are arranged at the second position that is the closest to a proximal end.

A basic configuration of the optical device according to the second modification of the embodiment of the present invention is substantially the same as the basic configurations of the aforementioned embodiment and the first modification. The optical device according to the second modification is different from the optical devices according to the aforementioned embodiment and the first modification in each of configurations of a yoke 34D that is a second magnetic body, a drive magnet 35D, a moving frame 32Dd including a magnet 36D that is a first magnetic body. Therefore, the same configurations as the configurations in the optical devices according to the aforementioned embodiment and the first modification will be denoted by the same reference signs, detailed description of the same configurations will be omitted, and only different configurations will be described in detail, in the following description regarding the optical device according to the second modification.

As illustrated in FIGS. 16 to 18, the optical device according to the second modification is an optical device having a so-called multi-focal-point switching function by which it is possible to perform switching setting of the focal length by a moving lens 32*b* of an optical system unit 32 moving in a direction along an optical axis O and being arranged at a predetermined position inside a distal end portion 6D. The optical device according to the second modification is illustratively described as a two-focal-point switching type optical device. Regarding the point, the optical device according to the second modification has the same configuration as the configurations of the optical devices according to the aforementioned embodiment and the first modification.

The yoke 34D that is the second magnetic body in the optical device according to the second modification is configured of a plurality of magnetic bodies. Here, the yoke 34D includes a plurality of magnetic bodies provided for each of a plurality of focal lengths that can be set by the optical system unit 32.

In other words, the yoke 34D includes two magnetic bodies, namely a first yoke 34Da by which the moving lens 32*b* and the drive unit are arranged at positions corresponding to the first position that is the closest to the distal end and a second yoke 34Db by which the moving lens 32*b* and the drive unit are arranged at positions corresponding to the second position that is the closest to the proximal end inside the distal end portion 6D of the endoscope to which the optical device according to the second modification is applied. The two magnetic bodies (yokes 34Da and 34Db) are provided in the same number as the number of focal lengths that the optical system unit 32 can set.

Each of the first yoke 34Da and the second yoke 34Db is formed into a substantially U shape. Also, each of the yokes 34Da and 34Db is provided in a form in which each of the yokes 34Da and 34Db surrounds an outer surface of a cleaning solution supply pipe 37. The first yoke 34Da and the second yoke 34Db are fixed to be separated from each other by a predetermined gap G (see FIG. 16) in an axis direction at predetermined positions that are close to the distal end of the cleaning solution supply pipe 37.

In the instance, each of distal ends of arm portions of the first yoke 34Da is arranged to face a first magnet 36Da (first magnetic body; which will be described later) of the moving frame 32Dd when the moving frame 32Dd is arranged at the first position. Each of distal ends of arm portions of the second yoke 34Db is arranged to face a second magnet 36Db (first magnetic body; which will be described later) of the moving frame 32Dd when the moving frame 32Dd is arranged at the second position.

Also, a bottom surface portion of the first yoke 34Da is arranged to be caused to face the first drive magnet 35Da (which will be described later) of the drive magnet 35D of the drive unit arranged at the first position. A bottom surface portion of the second yoke 34Db is arranged to be caused to face a second drive magnet 35Db (which will be described later) of the drive magnet 35D of the drive unit arranged at the second position.

Then, each of the yokes 34Da and 34Db is arranged such that a line of magnetic force M (see an arrow M in FIG. 16 and the like) passing through each of the yokes 34Da and 34Db has a predetermined inclination angle relative to the optical axis O of the optical system unit 32.

On the other hand, the drive magnet 35D in the optical device according to the second modification is configured of a plurality of magnets. Here, the drive magnet 35D includes a plurality of magnets provided for each of a plurality of focal lengths that can be set by the optical system unit 32.

In other words, the drive magnet 35D includes two magnets, namely a first drive magnet 35Da arranged at a position corresponding to the first position of the moving lens 32*b* and the first yoke 34Da when the drive unit is arranged at a first position that is the closest to the distal end and a second drive magnet 35Db arranged at a position corresponding to the second position of the moving lens 32*b* and the second yoke 34Db when the drive unit is arranged at a second position that is the closest to the proximal end inside the distal end portion 6D of the endoscope to which the optical device according to the second modification is applied. The two drive magnets (35Da, 35Db) are provided in the same number as the number of focal lengths that the optical system unit 32 can set.

The first drive magnet 35Da and the second drive magnet 35Db are fixed to be separated from each other by a predetermined gap W (see FIG. 16) in the axial direction at predetermined positions that are close to a distal end of a traction wire 35*w*. In the case, the first drive magnet 35Da is arranged to be caused to face the bottom surface portion of the first yoke 34Da when the drive unit is at the first position. The second drive magnet 35Db is arranged to be caused to face the bottom surface portion of the second yoke 34Db when the drive unit is at the second position. The two drive magnets (35Da, 35Db) are arranged such that the line of magnetic force M (see the arrow M in FIG. 16 and the like) outputted from each of the drive magnets (35Da, 35Db) has a predetermined inclination angle relative to the optical axis O of the optical system unit 32.

On the other hand, the magnet 36D (first magnetic body) provided at the moving frame 32Dd in the optical device according to the second modification includes a plurality of magnets. Here, the magnet 36D includes a plurality of magnets provided for each of the plurality of focal lengths that can be set by the optical system unit 32.

In other words, the magnet 36D provided at the moving frame 32Dd includes two magnets, namely a first magnet 36Da arranged at a position corresponding to the first yoke 34Da and the first drive magnet 35Da when the moving frame 32Dd and the drive unit are arranged at the first position that is the closest to the distal end and a second drive magnet 35Db arranged at a position corresponding to the second yoke 34Db and the second drive magnet 35Db when the moving frame 32Dd and the drive unit are arranged at the second position that is the closest to the proximal end inside the distal end portion 6D of the endoscope to which the optical device according to the second modification is applied. The two magnets (36Da, 36Db) are provided in the same number as the number of focal lengths that the optical system unit 32 can set.

The first magnet 36Da and the second magnet 36Db are fixed to be separated from each other at a predetermined gap W1 (see FIG. 16) in the axial direction on the outer surface of the moving frame 32Dd. In the case, the first magnet 36Da is arranged to be caused to face the distal end of the first yoke 34Da when the first yoke 34Da is arranged at the first position. Also, the second magnet 36Db is arranged to be caused to face the distal end of the second yoke 34Db when the second yoke 34Db is arranged at the second position. Each of the magnets (36Da, 36Db) is arranged such that each line of magnetic force M (see the arrow M in FIG. 16 and the like) outputted from each of the drive magnets (35Da, 35Db) and transmitted through each of the yokes (34Da, 34Db) has a predetermined inclination angle relative to the optical axis O of the optical system unit 32. In other words, it is only necessary for the yokes (the first yoke 34Da, the second yoke 34Db) to be arranged between the magnet 36D provided at the moving frame 32Dd and the drive magnets (the first drive magnet 35Da, the second drive magnet 35Db), and the arrangement is not limited to a position that is perpendicular to the optical axis O or on a strict straight line connecting the moving frame 32Dd and the drive magnets (35Da, 35Db). In other words, the yokes may be arranged at positions slightly deviating from the straight line connecting the moving frame 32Dd and the drive magnets (35Da, 35Db).

Also, each of the gap W between the first drive magnet 35Da and the second drive magnet 35Db, the gap G between the first yoke 34Da and the second yoke 34Db, and the gap W1 between the first magnet 36Da and the second magnet 36Db is set as follows.

First, when the moving frame 32Dd and the drive unit are at the first position, the first drive magnet 35Da, the first yoke 34Da. and the first magnet 36Da are arranged to be aligned on a substantially straight line as illustrated in FIG. 16. The line of magnetic force M from the first drive magnet 35Da is thus substantially straightly guided to the first magnet 36Da through the first yoke 34Da.

In the instance (when the moving frame 32Dd and the drive unit are at the first position), the second drive magnet 35Db is arranged at the intermediate position between the first yoke 34Da and the second yoke 34Db (see FIG. 16). When the second drive magnet 35Db is at the intermediate position, the magnetic force from the second drive magnet 35Db is not guided to the side of the magnet 36D of the moving frame 32Dd by any of the first yoke 34Da and the second yoke 34Db.

Therefore, only the magnetic force of the first drive magnet 35Da affects the magnet 36Da of the moving frame 32Dd in the case. It is thus possible to maintain the stable stopping state of the moving frame 32Dd at the first position by causing the movement of the drive unit to stop and maintaining the state in FIG. 16. Also, it is possible to cause the moving frame 32Dd to move in the same direction by causing the drive unit to move in the arrow X1 direction in FIG. 17.

On the other hand, when the moving frame 32Dd and the drive unit are at the second position, the second drive magnet 35Db, the second yoke 34Db. and the second magnet 36Db are arranged to be aligned on a substantially straight line as illustrated in FIG. 18. The line of magnetic force M from the second drive magnet 35Db is thus substantially straightly guided to the second magnet 36Db through the second yoke 34Db.

In the instance (when the moving frame 32Dd and the drive unit are at the second position), the first drive magnet 35Da is arranged at the intermediate position between the first yoke 34Da and the second yoke 34Db (see FIG. 18). When the first drive magnet 35Da is at the intermediate position, the magnetic force from the first drive magnet 35Da is not guided to the side of the magnet 36D of the moving frame 32Dd by any of the first yoke 34Da and the second yoke 34Db.

Therefore, only the magnetic force of the second drive magnet 35Db affects the magnet 36Db of the moving frame 32Dd in the case. It is thus possible to maintain a stable stopping state of the moving frame 32Dd at the second position by causing the movement of the drive unit to stop and maintaining the state in FIG. 18. Also, it is possible to cause the moving frame 32Dd to move in the same direction by causing the drive unit to move in the direction opposite to the arrow X1 in FIG. 17.

On the other hand, when the moving frame 32Dd and the drive unit are at the intermediate position between the first position (FIG. 16) and the second position (FIG. 18), the first drive magnet 35Da, a part of the first yoke 34Da, and the first magnet 36Da are arranged to be aligned on a substantially straight line, and the second drive magnet 35Db, a part of the second yoke 34Db, and the second magnet 36Db are arranged to be aligned on a substantially straight line as illustrated in FIG. 17.

In this manner, a part of the line of magnetic force M from the first drive magnet 35Da is straightly guided to the first magnet 36Da through the first yoke 34Da, and a part of the line of magnetic force M from the second drive magnet 35Db is straightly guided to the second magnet 36Db through the second yoke 34Db.

Therefore, the magnetic forces of both the first drive magnet 35Da and the second drive magnet 35Db affect the two magnets 36Da and 36Db of the moving frame 32Dd in the case. By causing the drive unit to move in the arrow X direction in FIG. 16, it is thus possible to cause the moving frame 32Dd to move in the same direction.

In short, the gap W between the first drive magnet 35Da and the second drive magnet 35Db, the gap G between the first yoke 34Da and the second yoke 34Db, and the gap W1 between the first magnet 36Da and the second magnet 36Db are set as follows.

In other words, setting is made such that it is possible to secure a state in which the magnetic force from the first drive magnet 35Da is smoothly transmitted to the first magnet 36Da and the magnetic force from the second drive magnet 35Db is not transmitted to the first magnet 36Da and the second magnet 36Db when the moving frame 32Dd and the drive unit are at the first position.

Also, setting is made such that it is possible to secure a state in which the magnetic force from the second drive magnet 35Db is smoothly transmitted to the second magnet 36Db and the magnetic force from the first drive magnet 35Da is not transmitted to the first magnet 36Da and the second magnet 36Db when the moving frame 32Dd and the drive unit are at the second position.

Also, setting is made such that it is possible to secure a state in which a part of the magnetic force from the first drive magnet 35Da is transmitted to the first magnet 36Da and a part of the magnetic force from the second drive magnet 35Db is transmitted to the second magnet 36Db when the moving frame 32Dd and the drive unit are at the intermediate position between the first position and the second position.

With the configuration, the line of magnetic force M from the drive magnet 35D is constantly guided to the magnet 36D and is not interrupted when the drive unit moves in the direction indicated by the arrow X in FIG. 16 between the first position that is the closest to the distal end and the second position that is the closest to the proximal end. In other words, the state in which the line of magnetic force M from the drive magnet 35D is constantly guided to the magnet 36D is maintained even when the moving frame 32Dd is at the intermediate position. The other configurations are the same as the configurations in the aforementioned embodiment.

Effects of the optical device according to the second modification with the configuration are as illustrated in FIGS. 16 to 18. FIG. 16 illustrates the state in which the moving lens 32*b* and the drive unit are arranged at the first position that is the closest to the distal end. When the moving lens 32*b* and the drive unit are arranged at the first position, the optical system unit 32 is set to have a first focal length out of two focal lengths that can be set.

In the state illustrated in FIG. 16, the drive unit is arranged at the first position that is the closest to the distal end. In the state, the line of magnetic force M from the first drive magnet 35Da is guided to the first magnet 36Da of the moving frame 32Dd through the first yoke 34Da. A magnetic force is thus generated among the first drive magnet 35Da, the first yoke 34Da, and the first magnet 36Da. Once the drive unit moves in the direction that is parallel to the optical axis O (the traction direction indicated by the arrow X) with the magnetic force, the moving lens 32*b* held by the moving frame 32Dd including the magnet 36D also moves in the same direction in conjunction with the movement.

Also, when the drive unit is at the first position, the moving lens 32*b* is also arranged at the first position. In the instance, the drive unit is in a stopping state at the first position. Thus, the moving lens 32*b* is in a stopping state at the corresponding first position due to an influence of the magnetic force of the drive magnet 35D. The stopping state of the moving lens 32*b* is maintained while the drive unit is stopped.

Next, once a predetermined operation on the operation lever 24 is performed, and the traction wire 35*w* of the drive unit is pulled in the predetermined traction direction (the arrow X1 direction in FIG. 17) in the state illustrated in FIG. 16, the drive magnet 35D moves in the same direction (the arrow X1 direction). Also, the drive magnet 35D moves to the position illustrated in FIG. 17.

As described above, FIG. 17 illustrates the state in which the moving lens 32*b* and the drive unit are arranged at the intermediate position between the first position and the second position. Once the drive unit moves from the first position in FIG. 16 to the intermediate position in FIG. 17, the moving lens 32*b* also moves from the first position in FIG. 16 to the intermediate position in FIG. 17.

In the instance, a part of the line of magnetic force M from the first drive magnet 35Da is guided through the first yoke 34Da, another part of the line of magnetic force M is guided through the second yoke 34Db, and both the parts are guided to the magnet 36D of the moving frame 32Dd. In other words, the line of magnetic force M from the drive magnet 35D is constantly continuously guided to the magnet 36D and is not interrupted when the drive unit moves from the first position in FIG. 16 to the second position in FIG. 18 via the intermediate position illustrated in FIG. 17. Therefore, when the drive unit moves in the arrow X1 direction, the moving frame 32Dd holding the moving lens 32*b* can also be continuously moved in the same direction in conjunction with the movement.

Next, if the drive unit further continues the movement in the arrow X1 direction via the state in FIG. 17, the state in FIG. 18 is eventually achieved. FIG. 18 illustrates the state in which the moving lens 32*b* and the drive unit are arranged at the second position that is the closest to the proximal end.

Once the movement of the drive unit is stopped at the second position illustrated in FIG. 18, the moving lens 32*b* also stops at the second position in FIG. 18. Then, the stopping state of the moving lens 32*b* is maintained while the drive unit is stopped. Thus, once the moving lens 32*b* is arranged at the second position in FIG. 18, the optical system unit 32 is set to have a second focal length out of the two focal lengths that can be set.

Effects in a case of transition from the state in FIG. 18 to the state in FIG. 16 via the state in FIG. 17 are substantially the same as the effects in the aforementioned case of the transition from the state in FIG. 16 to the state in FIG. 18 via the state in FIG. 17, and it is possible to perform switching setting of the focal length by the effects.

As described above, the moving frame 32Dd holding the moving lens 32*b* moves between the first position illustrated in FIG. 16 and the second position illustrated in FIG. 18 in the optical device according to the second modification. Then, when the drive unit is brought into the stopping state at each position out of the first position illustrated in FIG. 16 and the second position illustrated in FIG. 18, the stopping state of the moving frame 32Dd is fixed at each of the predetermined positions and the position is maintained until the operation of moving the drive unit is performed.

Also, the optical device according to the second modification is also configured to be provided with the plurality of (two) yokes (34Da, 34Db) in accordance with the focal lengths to be set. According to the configuration, the magnetic force of the first drive magnet 35Da and the magnetic force of the second drive magnet 35Db are efficiently guided to the respective magnets (36Da, 36Db) of the moving frame 32Dd at the first position and the second position, respectively, in the same manner as in the aforementioned first modification. It is thus possible to reliably maintain the stopping state of the moving frame 32Dd at each position out of the first position and the second position.

Furthermore, the optical device according to the second modification can more efficiently transmit the magnetic force of the drive magnet 35D since arrangement of each configuration member is devised to cause the line of magnetic force M to be inclined relative to the optical axis O. It is thus possible to increase a propelling force of the moving frame 32Dd in the direction along the optical axis O. The increase can contribute to securing of the movement of the moving frame 32Dd in the optical axis O direction even if an arrangement distance between the optical system unit 32 and the drive magnet 35D increases.

Note that although the example in which all the magnet 36D (first magnetic body) of the moving frame 32Dd, the yoke 34D (second magnetic body), and the drive magnet 35D are arranged such that the line of magnetic force M is inclined relative to the optical axis O has been described as the configuration in the aforementioned second modification, the present invention is not limited to the configuration example. It is only necessary for at least one of the magnet 36D (first magnetic body) of the moving frame 32Dd, the yoke 34D (second magnetic body), or the drive magnet 35D to be set in the arrangement in which the line of magnetic force M is inclined relative to the optical axis O, for example, in the second modification.

Also, although the example in which the magnet 36D that the moving frame 32Dd includes is configured of a member that is separated from the moving frame 32Dd has been described as the configuration in the aforementioned second modification, the present invention is not limited to the configuration example. For example, partially configuring a predetermined part of the moving frame 32Dd as a magnetic body is conceivable (see the example of the form as illustrated in FIG. 4B).

Figure 18A:
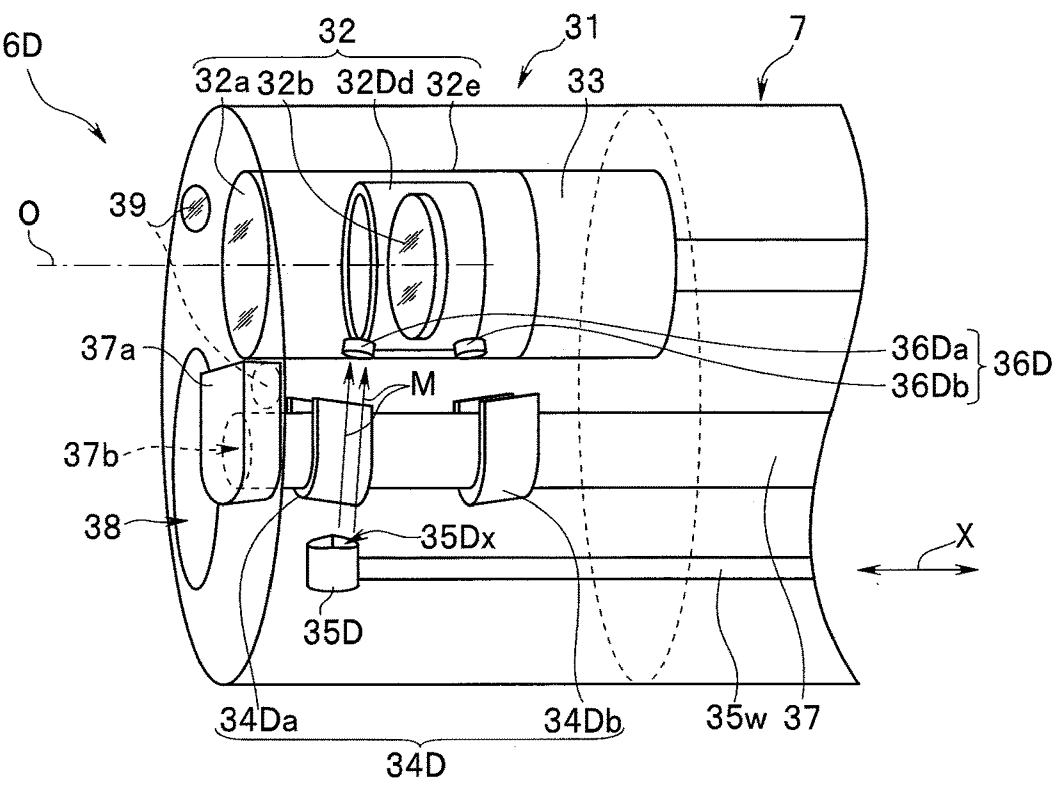
FIG. 18A is a diagram illustrating a further modification of the second modification of the embodiment of the present invention (a state where the moving lens and the drive magnet are arranged in the first position)
Figure 18B:
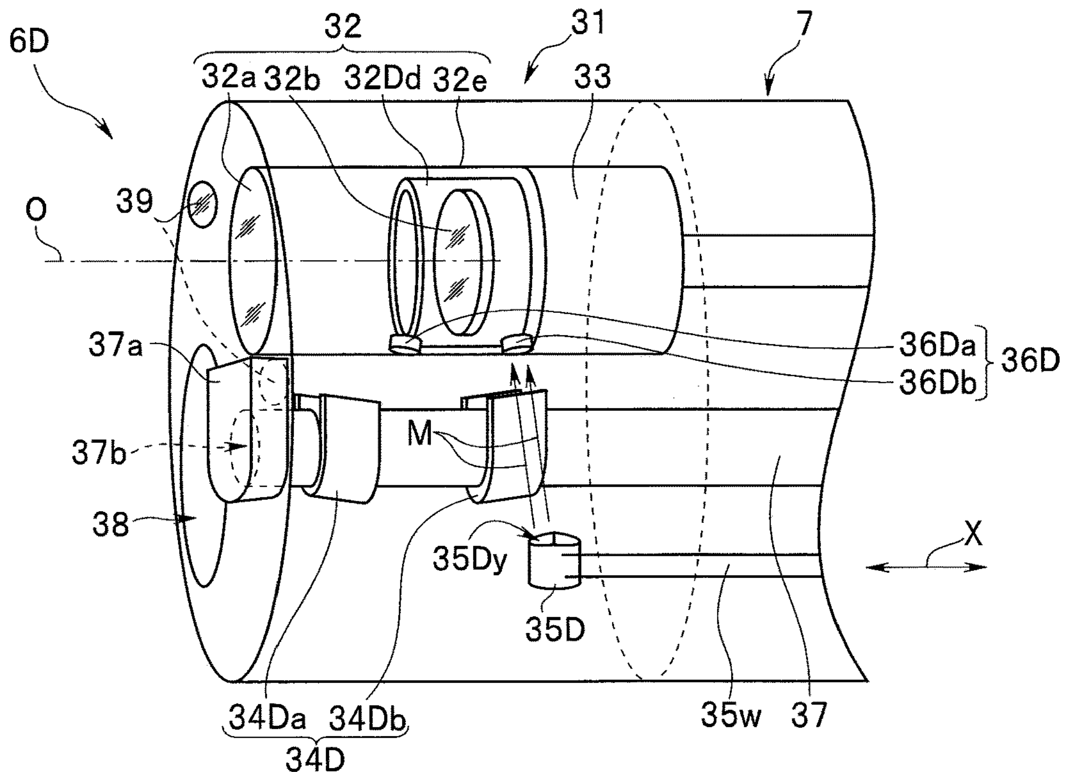
FIG. 18B is a diagram illustrating a state where the moving lens and the drive magnet have moved in the optical axis direction from the state in FIG. 18A and have been arranged in the second position.

For example, FIGS. 18A and 18B illustratively describe a yet further modification. The modification is configured by arranging only one drive magnet 35D at a distal end of a traction wire 35*w* as illustrated in FIGS. 18A and 18B. The drive magnet 35D is configured to freely advance and retract in an arrow X direction illustrated in FIGS. 18A and 18B by an operation of the traction wire 35*w*. In other words, the drive magnet 35D moves between a first position aligned with a first yoke 34Da and a first magnet 36Da with a first inclination angle relative to an optical axis O of an optical system unit 32 as illustrated in FIG. 18A and a second position aligned with a second yoke 34Db and a second magnet 36Db with a second inclination angle relative to the optical axis O of the optical system unit 32 as illustrated in FIG. 18B.

In the case, the drive magnet 35D includes a first surface 35Dx (see FIG. 18A) facing the first yoke 34Da when the drive magnet 35D is aligned with the first yoke 34Da with the first inclination angle and a second surface 35Dy (see FIG. 18B) facing the second yoke 34Db when the drive magnet 35D is aligned with the second yoke 34Db with the second inclination angle.

According to the configuration, the line of magnetic force M is emitted on a straight line from the first surface 35Dx of the drive magnet 35D and reaches the first magnet 36Da through the first yoke 34Da when the drive magnet 35D is at the first position illustrated in FIG. 18A.

Also, the line of magnetic force M is emitted on a straight line from the second surface 35Dy of the drive magnet 35D and reaches the second magnet 36Db through the second yoke 34Db when the drive magnet 35D is at the second position illustrated in FIG. 18B.

As a form that is different from the aforementioned modification, another modification as follows is also conceivable (however, only description will be given, and illustration will be omitted). In other words, a drive magnet 35D is configured to have a rotation shaft, and the rotation shaft is supported at a distal end portion of a traction wire 35*w*. In the instance, the rotation shaft is arranged to perpendicularly intersect a long axis direction of the traction wire 35*w*. The drive magnet 35D is thus configured to rotate within a predetermined angular range about the rotation shaft at the distal end portion of the traction wire 35*w*. Furthermore, the drive magnet 35D includes a first surface 35Dx and a second surface 35Dy in the case similarly to the illustration in FIGS. 18A and 18B.

According to the modification with such a configuration, once the traction wire 35*w* is operated, and the drive magnet 35D is caused to move in the arrow X direction similarly to FIG. 18A and the like, the drive magnet 35D moves to a first position facing a first yoke 34Da and a second position facing a second yoke 34Db. Then, the first surface 35Dx faces the first yoke 34Da when the drive magnet 35D is at the first position, and the second surface 35Dy faces the second yoke 34Db when the drive magnet 35D is at the second position.

Incidentally, the observation unit and the drive unit are configured as separated members in the optical devices illustratively described in the aforementioned embodiment, each of the modifications, and the like. A significant advantage that the configuration can further contribute to an improvement in maintainability is achieved in addition to the aforementioned various effects and advantages (for example, an improvement in a degree of freedom in arranging members inside the distal end portion).

A case in which a defect occurs in any of the plurality of configuration units (for example, the observation unit, the drive unit, the cleaning unit, the illumination unit, the treatment instrument channel, and the like) disposed at the distal end portion in the endoscope to which the optical device is applied and a so-called maintenance work such as replacement/repair of the defect member in the endoscope is needed, for example, will be considered.

In the case, it is only necessary to perform a replacement work or the like of only the configuration unit in which the defect has occurred, and configuration units in which no defect has been discovered can be continuously used without any work in the endoscope to which the optical device according to the embodiment of the present invention illustratively described in FIG. 4A and the like is applied, for example.

On the other hand, if a defect occurs in one of the observation unit and the drive unit and no problem has occurred in the other, for example, in an endoscope to which an optical device in the conventional form with the observation unit and the drive unit integrally configured is applied, a maintenance work of taking out and replacing the optical device with the integrated configuration occurs. Thus, the endoscope to which the optical device of the present invention with the observation unit and the drive unit configured as separated members can contribute to an improvement in maintainability.

In addition, in a third modification of the present embodiment described below, a drive unit, in particular, is split into each allocated function (for example, a traction function, a guide function, and the like) and configures individual configuration units, and a combination of the plurality of configuration units configures the drive unit. With the configuration, the third modification further contributes to an improvement in maintainability of an optical device. Hereinafter, the configuration of the optical device according to the third modification will be described.

Figure 19:
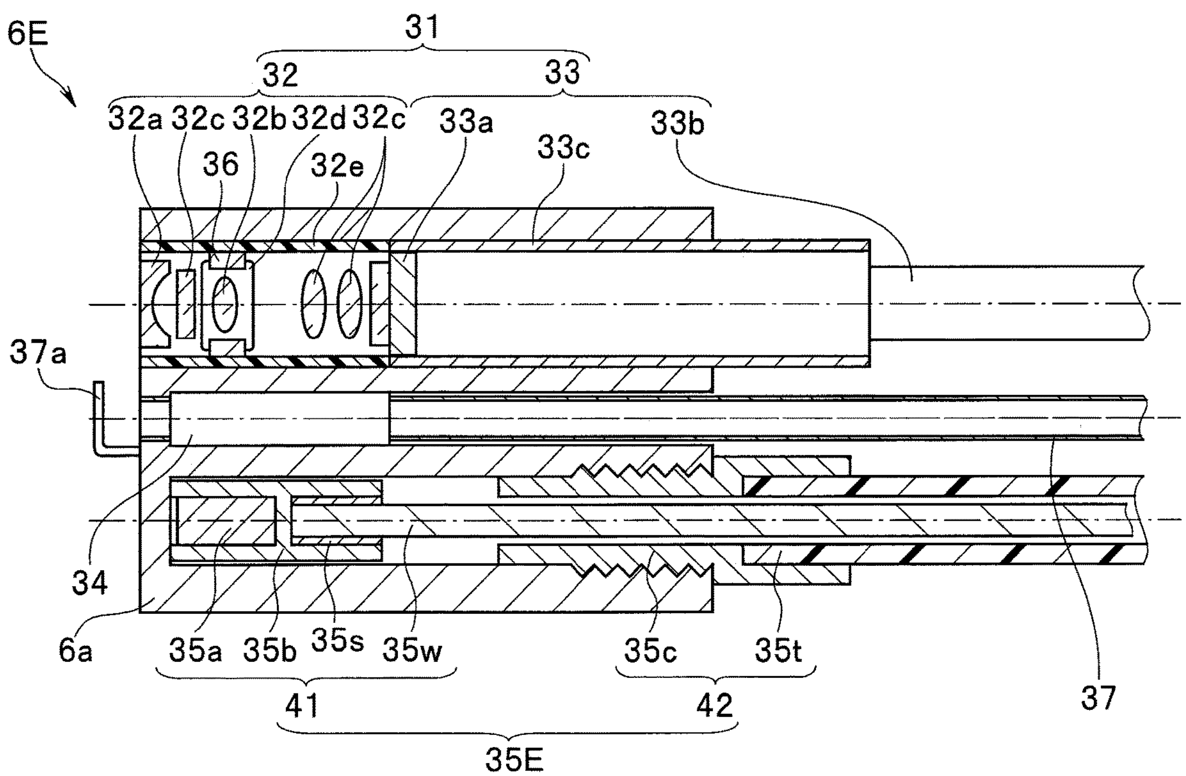
FIG. 19 is a schematic sectional view conceptually illustrating a configuration of a distal end portion of an endoscope to which an optical device according to a third modification of the embodiment of the present invention is applied (a sectional view corresponding to a section taken along a line [4]-[4] in FIG. 3)

FIG. 19 is a conceptual sectional view conceptually illustrating a configuration of a distal end portion of an endoscope to which the optical device according to the third modification of the present embodiment is applied. Note that FIG. 19 illustrates a section along the line [4]-[4] in FIG. 3.

Figure 20:
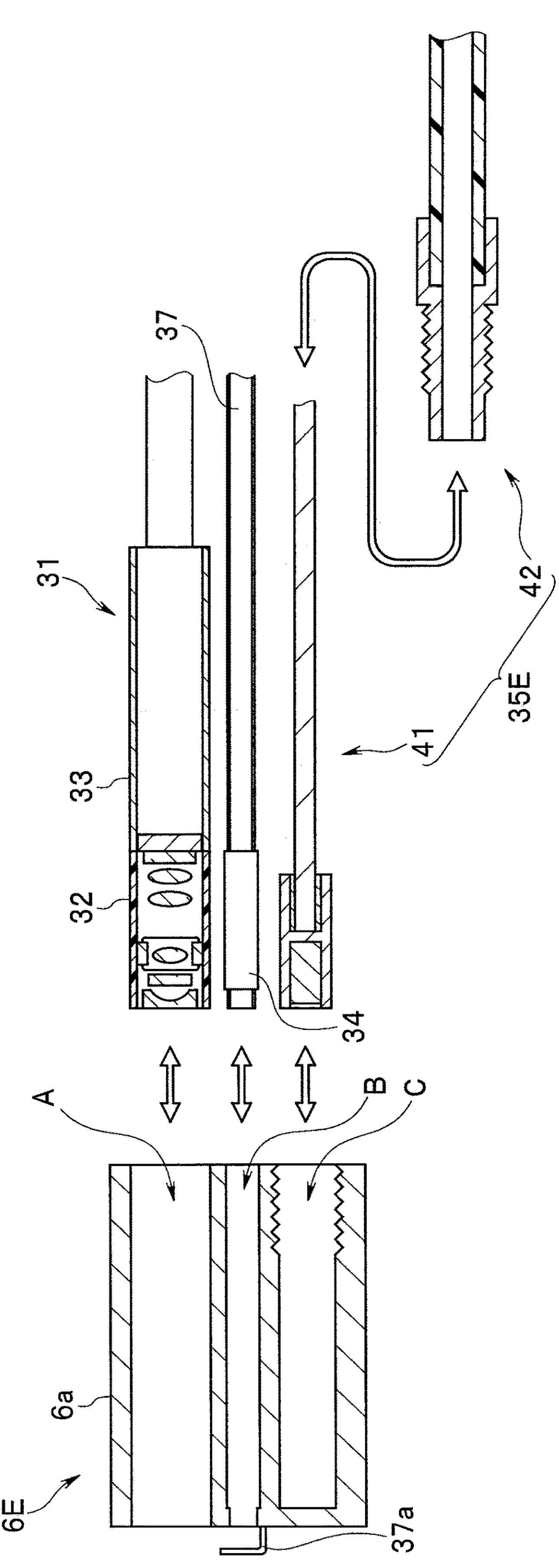
FIG. 20 is a conceptual diagram illustrating each configuration unit of the distal end portion of the endoscope in FIG. 19 in a separated manner.

FIG. 20 is a conceptual diagram illustrating each configuration unit of the distal end portion of the endoscope in FIG. 19 in a separated manner.

A basic configuration of the third modification of the embodiment of the present invention is substantially the same as the basic configuration in the aforementioned embodiment as illustrated in FIG. 19. The optical device according to the third modification is slightly different from the optical device according to the aforementioned embodiment in a configuration of a drive unit 35E. Therefore, the same configurations as the configurations in the optical device according to the aforementioned embodiment will be denoted by the same reference signs, detailed description of the same configurations will be omitted, and only different configurations (mainly, the drive unit 35E) will be described in detail, in the following description regarding the optical device according to the third modification.

The drive unit 35E according to the third modification is configured of two configuration units, namely a traction portion 41 and a guide portion 42. The traction portion 41 includes a drive magnet 35*a*, a traction wire 35*w*, and a holding member 35*b*. Here, the holding member 35*b* is a configuration member that holds the drive magnet 35*a* at a part that is close to a distal end and fixes a distal end of the traction wire 35*w* to a part that is close to a rear end. Therefore, the holding member 35*b* is formed of a ferromagnetic material that does not inhibit a magnetic force of the drive magnet 35*a*. Also, fixing means using a solder 35*s*, for example, is applied as means for fixing the distal end of the traction wire 35*w* to the holding member 35*b* in order to secure strength.

The guide portion 42 includes a fixing member 35*c* and a guide pipe 35*t*. The fixing member 35*c* is formed to have a through-hole penetrating in a long axis direction and is formed into a cylindrical shape as a whole. The fixing member 35*c* is fixed with a screw, for example, to a main body 6*a* of a distal end portion 6E. Therefore, a male screw is formed on an outer circumferential surface of the fixing member 35*c* near the distal end. Correspondingly, a female screw into which the male screw of the fixing member 35*c* is screwed is formed at a predetermined position (a part where the drive unit 35E is disposed) of the main body 6*a* of the distal end portion 6E near the proximal end. Also, a distal end of the guide pipe 35*t* (guide tube) is fixed to the side of the proximal end of the fixing member 35*c*.

The guide pipe 35*t* is an elongated pipe-shaped member formed by using a resin material with flexibility and excellent bending resistance, such as polyether ether ketone (PEEK), for example. The traction wire 35*w* is inserted into the inside of the guide pipe 35*t* such that the traction wire 35*w* is slidable in the long axis direction. Thus, the guide pipe 35*t* functions as a guide tube guiding the traction wire 35*w*. The other configurations are substantially the same as the configurations in the aforementioned embodiment.

In the third modification with the configuration, each configuration unit (the observation unit 31, the drive unit 35E) configuring the optical device and each configuration unit (the cleaning unit including the cleaning solution supply pipe 37 and the yoke 34, the illumination unit and the treatment instrument channel that are not illustrated, and the like) configuring the endoscope are removably assembled with each predetermined part of the main body 6*a* of the distal end portion 6E as illustrated in FIG. 20.

For example, the observation unit 31 (the optical system unit 32 and the image pickup unit 33 are integrally configured) is removably assembled with a part indicated by reference sign A in the main body 6*a* of the distal end portion 6E. Also, the cleaning unit (the cleaning solution supply pipe 37, the cleaning nozzle 37*a*, and the yoke 34 (first magnetic body)) are removably assembled with a part indicated by reference sign B in the main body 6*a* of the distal end portion 6E. In the case, the cleaning solution supply pipe 37 and the yoke 34 are integrally configured to be detachable, and the cleaning nozzle 37*a* is provided as a separated configuration at the front surface of the main body 6*a* of the distal end portion 6E, in the cleaning unit. Separately from the configuration, it is also possible to employ a form in which the cleaning nozzle 37*a* is configured integrally with the distal end of the cleaning solution supply pipe 37.

The drive unit 35E is removably assembled with a part indicated by reference sign C in the main body 6*a* of the distal end portion 6E. Here, the traction portion 41 and the guide portion 42 are configured as separated members as described above in the drive unit 35E. Therefore, it is possible to replace any one of the configuration units, namely the traction portion 41 or the guide portion 42 and to continuously use the other configuration unit in the drive unit 35E at the time of maintenance or the like.

Furthermore, although illustration is omitted, the illumination unit and the treatment instrument channel are also configured to be removably assembled with predetermined parts of the main body 6*a* of the distal end portion 6E.

According to the aforementioned configuration, each of the configuration units such as the observation unit 31, the cleaning unit, the illumination unit, the treatment instrument channel, and the like can be appropriately detached from the distal end portion 6E and can be easily replaced at the time of maintenance or the like.

As described above, according to the optical device of the third modification, it is possible to repair and replace only a unit in which a defect has occurred when the defect occurs only in the traction portion 41 or only in the guide portion 42 of the drive unit 35E, for example, and a work such as replacement/repair or the like is needed. In the case, the other configuration unit in which no defect has occurred can be used again.

Therefore, the configuration according to the third modification contributes to an improvement in maintainability and can enable efficient running of the device. Additionally, the configuration according to the third modification can contribute to saving of maintenance costs and running costs of the device.

Furthermore, according to the third modification, it is possible to easily develop a variety (variations) commonly including the configuration units, to contribute to simplification of the maintenance work, thereby to contribute to an improvement in maintenance management performance, and to contribute to reduction of manufacturing costs.

It is a matter of course that the present invention is not limited to the aforementioned embodiment and various modifications and applications can be made without departing from the gist of the invention. Furthermore, the above embodiment includes the invention in various levels, and various inventions can be extracted by appropriately combining a plurality of constituent elements disclosed. For example, in a case in which the problem to be solved by the invention can be solved and the advantages of the invention can be obtained even if some constituent elements are deleted from among all the constituent elements described in the above embodiment, a configuration obtained by deleting the constituent elements can be extracted as an invention. Furthermore, components in different embodiments may be appropriately combined. The invention is limited only by the accompanying claims and is not constrained by specific embodiments of the invention.

What is claimed is:

1. An optical device comprising:

an optical system including a moving lens that moves in a direction along an optical axis;

a moving frame including a first magnetic body and configured to hold the moving lens;

a holding frame formed into a cylindrical shape by a non-magnetic body and configured to movably hold the moving frame on an inner circumferential surface along the optical axis;

a drive unit including a magnet and configured to cause the moving frame to move in the direction along the optical axis by moving in the direction along the optical axis in response to an external operation; and second magnetic bodies arranged between the drive unit and the moving frame, configured to transmit a first magnetic force of the magnet to the first magnetic body of the moving frame, and provided in a same number as a number of focal points that can be set as adjustment targets of the optical system;

wherein the drive unit causes the moving frame to move in the optical axis direction by a second magnetic force generated among the magnet and the first magnetic body through the second magnetic bodies.

2. The optical device according to claim 1, wherein the number of the second magnetic bodies provided is same as a number of focal lengths that the optical system can set.

3. The optical device according to claim 1, wherein at least one of the first magnetic body, the second magnetic bodies, or the magnet is set in an arrangement in which a line of magnetic force is inclined relative to the optical axis.

4. The optical device according to claim 1, wherein the second magnetic bodies include an open magnetic path structure with one end portion magnetically opened, and open ends of the second magnetic bodies are arranged to face the first magnetic body.

5. The optical device according to claim 4, wherein the second magnetic bodies are formed in a U shape.

6. The optical device according to claim 1, wherein the moving frame is formed of a material with magnetism, and the moving frame itself is configured as the first magnetic body.

7. An endoscope comprising:

an optical system including a moving lens that moves in a direction along an optical axis;

a moving frame including a first magnetic body and configured to hold the moving lens;

a holding frame formed into a cylindrical shape by a non-magnetic body and configured to movably hold the moving frame on an inner circumferential surface along the optical axis;

a drive unit including a magnet and configured to cause the moving frame to move in the direction along the optical axis by moving in the direction along the optical axis in response to an external operation;

second magnetic bodies arranged between the drive unit and the moving frame, configured to transmit a first magnetic force of the magnet to the first magnetic body of the moving frame, and provided in a same number as a number of focal points that can be set as adjustment targets of the optical system; and a conduit line or an illumination device arranged between the drive unit and the moving frame;

wherein the drive unit causes the moving frame to move in the optical axis direction by a second magnetic force generated among the magnet and the first magnetic body through the second magnetic bodies.

8. The endoscope according to claim 7, wherein the number of the second magnetic bodies provided is same as a number of focal lengths that the optical system can set.

9. The endoscope according to claim 7, wherein the second magnetic bodies are arranged in a form in which the second magnetic bodies surround an outer circumference of the conduit line or the illumination device.

10. The endoscope according to claim 7, wherein at least one of the first magnetic body, the second magnetic bodies, or the magnet is set in an arrangement in which a line of magnetic force is inclined relative to the optical axis.

11. The endoscope according to claim 7, wherein the second magnetic bodies include an open magnetic path structure with one end portion magnetically opened, and distal ends of the second magnetic bodies are arranged to face the first magnetic body.

12. The endoscope according to claim 11, wherein the second magnetic bodies are formed in a U shape.

13. The endoscope according to claim 7, wherein the first magnetic body, the second magnetic bodies, and the magnet are linearly arranged along a line of magnetic force.

14. The endoscope according to claim 7, wherein the conduit line includes, at a distal end, a cleaning nozzle configured to spray a cleaning solution toward a front surface of the optical system.

15. The endoscope according to claim 7, wherein the drive unit includes a traction member coupled to the magnet, a guide tube into which the traction member is inserted, and a fixing member configured to fix a distal end of the guide tube, and the moving frame is caused to move in the direction along the optical axis by causing the traction member to move in the direction along the optical axis relative to the guide tube in a state where the distal end of the guide tube is fixed to the fixing member.

16. The endoscope according to claim 7, wherein the moving frame is formed of a material with magnetism, and the moving frame itself is configured as the first magnetic body.

17. An optical device comprising:

an optical system including a moving lens that moves in a direction along an optical axis;

a moving frame including a first magnetic body and configured to hold the moving lens;

a holding frame formed into a cylindrical shape by a non-magnetic body and configured to movably hold the moving frame on an inner circumferential surface along the optical axis;

a drive unit including a magnet and configured to cause the moving frame to move in the direction along the optical axis; and second magnetic bodies arranged between the drive unit and the moving frame, configured to transmit a magnetic force of the magnet to the first magnetic body of the moving frame, and provided in a same number as a number of focal points that can be set as adjustment targets of the optical system;

wherein the second magnetic bodies include an open magnetic path structure with one end portion magnetically opened, and open ends of the second magnetic bodies are arranged to face the first magnetic body.

18. An endoscope comprising:

an optical system including a moving lens that moves in a direction along an optical axis;

a moving frame including a first magnetic body and configured to hold the moving lens;

a holding frame formed into a cylindrical shape by a non-magnetic body and configured to movably hold the moving frame on an inner circumferential surface along the optical axis;

a drive unit including a magnet and configured to cause the moving frame to move in the direction along the optical axis;

second magnetic bodies arranged between the drive unit and the moving frame, configured to transmit a magnetic force of the magnet to the first magnetic body of the moving frame, and provided in a same number as a number of focal points that can be set as adjustment targets of the optical system; and a conduit line or an illumination device arranged between the drive unit and the moving frame;

wherein the second magnetic bodies are arranged in a form in which the second magnetic bodies surround an outer circumference of the conduit line or the illumination device.

19. An endoscope comprising:

an optical system including a moving lens that moves in a direction along an optical axis;

a moving frame including a first magnetic body and configured to hold the moving lens;

a holding frame formed into a cylindrical shape by a non-magnetic body and configured to movably hold the moving frame on an inner circumferential surface along the optical axis;

a drive unit including a magnet and configured to cause the moving frame to move in the direction along the optical axis;

second magnetic bodies arranged between the drive unit and the moving frame, configured to transmit a magnetic force of the magnet to the first magnetic body of the moving frame, and provided in a same number as a number of focal points that can be set as adjustment targets of the optical system; and a conduit line or an illumination device arranged between the drive unit and the moving frame;

wherein the second magnetic bodies include an open magnetic path structure with one end portion magnetically opened, and distal ends of the second magnetic bodies are arranged to face the first magnetic body.

* * * * *